United States Patent
Saghafi et al.

(10) Patent No.: US 11,298,071 B1
(45) Date of Patent: Apr. 12, 2022

(54) MACHINE LEARNING ANALYTICS IN REAL TIME FOR HEALTH SERVICES

(71) Applicant: University of South Florida, Tampa, FL (US)

(72) Inventors: Abolfazl Saghafi, Tampa, FL (US); Chris P. Tsokos, Tampa, FL (US)

(73) Assignee: University of South Florida, Tampa, FL (US)

( * ) Notice: Subject to any disclaimer, the term of this patent is extended or adjusted under 35 U.S.C. 154(b) by 658 days.

(21) Appl. No.: 16/161,975

(22) Filed: Oct. 16, 2018

Related U.S. Application Data

(60) Provisional application No. 62/572,782, filed on Oct. 16, 2017.

(51) Int. Cl.
| | |
|---|---|
| *A61B 5/00* | (2006.01) |
| *A61B 5/24* | (2021.01) |
| *A61B 5/372* | (2021.01) |
| *G06F 17/18* | (2006.01) |
| *G06N 7/00* | (2006.01) |
| *A61B 5/316* | (2021.01) |

(52) U.S. Cl.
CPC .............. *A61B 5/4076* (2013.01); *A61B 5/24* (2021.01); *A61B 5/2415* (2021.01); *A61B 5/316* (2021.01); *A61B 5/725* (2013.01); *G06F 17/18* (2013.01); *G06N 7/00* (2013.01)

(58) Field of Classification Search
None
See application file for complete search history.

(56) References Cited

U.S. PATENT DOCUMENTS

| | | |
|---|---|---|
| 8,437,844 B2 | 5/2013 | Syed Momen et al. |
| 9,547,821 B1 | 1/2017 | Loreggia et al. |
| 10,357,163 B1 * | 7/2019 | Selvaraj ............... A61B 5/7207 |

(Continued)

OTHER PUBLICATIONS

Gallego-Jutgla et al. Application of multivariate empirical mode decomposition for cleaning eye blinks artifacts from EEG signals. International Conference on Neural Computation Theory and Applications, Jan. 2011. (Year: 2011).*

(Continued)

*Primary Examiner* — Etsub D Berhanu
(74) *Attorney, Agent, or Firm* — Meunier Carlin & Curfman LLC

(57) ABSTRACT

Methods and systems detect a random state change in a subject in real time. Eye state changes may be identified in encephalogram brain signals, or honeybee dance patterns may be classified. Multivariate signals including state change information are received via a plurality of channels. The signals are sampled and may be filtered to remove DC components. Statistical characteristics of the signals are monitored. When the statistical characteristics exceed a threshold during a critical time interval, a potential change of state is detected. The critical time segment of the signals may be filtered to generate respective state change artifact signals. The state change artifact signals are decomposed by MEMD, and intrinsic mode functions are generated. Features are extracted from the intrinsic mode functions. These steps may be repeated while the extracted features are provided to a logistic regression classifier that is used to predict a state of the subject.

20 Claims, 15 Drawing Sheets
(15 of 15 Drawing Sheet(s) Filed in Color)

(56) References Cited

U.S. PATENT DOCUMENTS

| | | | | |
|---|---|---|---|---|
| 2010/0109881 | A1* | 5/2010 | Eskandarian | A61B 5/7267 340/575 |
| 2011/0257556 | A1* | 10/2011 | Guo | A61B 5/4812 600/544 |
| 2014/0228701 | A1* | 8/2014 | Chizeck | G06F 21/6254 600/544 |
| 2015/0216468 | A1 | 8/2015 | Vidal-Naquet et al. | |
| 2015/0293143 | A1* | 10/2015 | Zao | G01C 22/006 702/19 |
| 2017/0061282 | A1 | 3/2017 | Ryskamp | |
| 2017/0188891 | A1* | 7/2017 | Lin | A61B 5/113 |

OTHER PUBLICATIONS

Sabanci et al. The Classification of Eye State by Using kNN and MLP Classification Models According to the EEG Signals. International Journal of Intelligent Systems and Applications in Engineering, Dec. 2015. (Year: 2015).*

Wang et al. The Removal of EOG Artifacts from EEG Signals Using Independent Component Analysis and Multivariate Empirical Mode Decomposition. IEEE Journal of Biomedical and Health Information, vol. 20, No. 5, Sep. 2016. (Year: 2016).*

Narejo et al. EEG Based Eye State Classification using Deep Belief Network and Stacked AutoEncoder. International Journal of Electrical and Computer Engineering, vol. 6, n. 6, pp. 3131-3141, 2016. (Year: 2016).*

Roesler et al. Comparison of EEG Devices for Eye State Classification. (Year: 2014).*

FAO (2015) Agricultural Statistics, Accessed May 2017, www.faostat.fao.org/site/567/default.aspx.

Fox, "Bayesian Nonparaetric Learning of Complex Dynamical Phenomena," Doctoral Thesis, Massachusetts Institute of Technology, Jul. 2009.

Landgraf et al., "Analysis of the waggle dance motion of honeybees for the design of a biomimetic honeybee robot," PLoS ONE, 2011, 6(8): e21354, 10 pages.

Mileros, "A real time classification approach of human brain-computer interface based on movement related electroencephalogram," Thesis, Institute of Technology at Linkoping University, 2004, 90 pages.

Morse et al., "The value of honey bees as pollinators of US crops in 2000," Bee Culture, 2000, 128, 1-15.

Oh et al., "Learning and Inferring Motion Patterns using Parametric Segmental Switching Linear Dynamic Systems," International Journal of Computer Vision (IJCV) Special Issue on Learning for Vision, 2008, 77(1-3), 103-124.

Rösler et al., "First step towards eye state prediction using EEG," Proc. International Conference on Applied Informatics for Health and Life Sciences (AIHLS 13), Istanbul, Turkey, Sep. 2013, 4 pages.

Sabanci et al., "The Classification of Eye State by Using kNN and MLP Classification Models According to the EEG Signals," International Journal of Intelligent Systems and Applications in Engineering, 2015, 3(4), 127-130.

Saghafi et al., "Common spatial pattern metthod for real-time eye state identification by using electroencephalogram signals," The Institute of Engineering and Technology, 2017, 6 pages.

Saghafi et al., "Random eye state change detection in real-time using EEG signals," Expert Systems with Applications, 2017, vol. 72, pp. 42-48.

Saghafi et al., "Real-time Classification of Biomedical Signals, Parkinson's Analytical Model," Graduate Theses and Dissertations, 2017, 101 pages.

Wang et al., "EEG Eye State Identification Using Incremental Attribute Learning with Time-Series Classification," Mathematical Problems in Engineering. 2014(2014), 158-161.

Xuan et al., "Modeling changing dependency structure in multivariate time series," Proc. of International Conference on Machine Learning, Jun. 2007, pp. 1055-1062.

* cited by examiner a b (c) sample honey bee dance #6

(b) sample honey bee dance #5

(a) sample honey bee dance #1

Honeybee dance patterns, turn-right (blue), turn-left (green), waggle (red)

MACHINE LEARNING ANALYTICS IN REAL TIME FOR HEALTH SERVICES

CROSS-REFERENCE TO RELATED APPLICATIONS

This application is a non-provisional of and claims the benefit of U.S. Provisional Application No. 62/572,782, filed on Oct. 16, 2017, the contents of which are incorporated herein by reference.

BACKGROUND OF THE INVENTION

One of the drawbacks of employing machine learning analytics is that most state-of-the-art algorithms require extensive training and prediction times, thus they are not suitable for real-time predictions, which limit their real-life applications.

SUMMARY OF THE INVENTION

A method is disclosed for detecting a random state change in a physical subject. A plurality of multivariate signals is received via a respective plurality of physical channels. The plurality of multivariate signals includes information about a state change in the physical subject. The multivariate signals are sampled at a specified sampling rate. In some embodiments, the multivariate signals are processed in a high pass filter to remove DC components. Statistical characteristics of the plurality of multivariate signals are monitored. A potential change of state in the physical subject is detected when the monitored statistical characteristics exceed a threshold during a critical time interval of the plurality of multivariate signals. The critical time segment of the plurality of multivariate signals may be filtered to generate a respective plurality of state change artifact signals.

The plurality of state change artifact signals may be simultaneously decomposed by multivariate empirical mode decomposition (MEMD) and a plurality of intrinsic mode functions may be generated. Features may be extracted from one or more of the plurality of intrinsic mode functions. The steps of monitoring, detecting, low-pass filtering, and decomposing may be repeated and the extracted features may be provided to a logistic regression classifier. A state of the physical subject may be predicted using a logistic regression classifier.

In some embodiments the plurality of multivariate signals are high passed filtered to remove DC components of the plurality of multivariate signals prior to the monitoring of the values of the statistical characteristics of the plurality of multivariate signals.

In some embodiments the physical subject is an eye and potential states of the eye include an open state and a closed state.

In some embodiments the physical subject is a honeybee dance and potential states of the honeybee dance are a right turn state, a left turn state, and a waggle state.

In some embodiments the plurality of multivariate signals are nonlinear and non-stationary signals.

In some embodiments the statistical characteristics of the plurality of multivariate signals include maximum and minimum values of the plurality of multivariate signals.

In some embodiments the statistical characteristics of the plurality of multivariate signals are monitored at a reduced rate relative to the sampling rate.

In some embodiments the respective plurality of state change artifact signals are eye opening or eye closing artifact signals.

In some embodiments the features are extracted from the one or more of the plurality of intrinsic mode functions over a reduced time interval relative to the critical time interval.

In some embodiments the features are extracted from one or more of the plurality of intrinsic mode functions over a reduced time interval relative to the critical time interval, using a common spatial pattern method.

In some embodiments the features are extracted from one or more of the plurality of intrinsic mode functions over a reduced time interval relative to the critical time interval, based on values of discriminant features of the one or more intrinsic mode functions.

A system is disclosed for detecting a random state change in a physical subject, the system may include a high pass filter that removes DC components of a plurality of multivariate signals and generates a respective plurality of first filtered signals. The system also includes a potential change of state detector that monitors values of statistical characteristics of the plurality of first filtered signals and detects a change of state when the statistical characteristics values exceed a threshold during a critical time interval of the plurality of first filtered signals. A low-pass filter of the system filters the critical time segment of the plurality of first filtered signals to generate a respective plurality of state change artifact signals. A multivariate empirical mode decomposer of the system simultaneously decomposes the plurality of state change artifact signals and generates a respective plurality of intrinsic mode functions. A feature extractor of the system evaluates discriminant features of one or more of the plurality of intrinsic mode functions. A logistic regression classifier predicts a state of the physical subject matter.

A system for detecting a random state change in a physical subject, the system includes a memory storing program instructions, and one or more electronic processors coupled to the memory. The one or more electronic processors, through retrieval and execution of the program instructions, configured to receive a plurality of multivariate signals via a respective plurality of physical channels, wherein the plurality of multivariate signals comprise information about the state change in the physical subject. The one or more electronic processors sample the plurality of multivariate signals at a specified sampling rate. Values of statistical characteristics of the plurality of multivariate signals are monitored. A potential change of state in the physical subject is detected when the monitored statistical characteristics values of the plurality of multivariate signals exceed a threshold during a critical time interval of the plurality of multivariate signals. The critical time segment of the plurality of multivariate signals is low passed filtered to generate a respective plurality of state change artifact signals. The one or more electronic processors simultaneously decompose the plurality of state change artifact signals by multivariate empirical mode decomposition and generate a plurality of intrinsic mode functions. The one or more electronic processors extract features from one or more of the plurality of intrinsic mode functions and provide the features to a logistic regression classifier. The electronic processor repeats the steps of monitoring, detecting, low-pass filtering, decomposing, extracting, and providing the extracted features to the logistic regression classifier. The electronic processor predicts a state of the physical subject using the logistic regression classifier.

In some embodiments the electronic processor high pass filters the plurality of multivariate signals to remove DC components of the plurality of multivariate signals prior to the monitoring of the values of the statistical characteristics of the plurality of multivariate signals.

In some embodiments the physical subject is an eye and potential states of the eye include an open state and a closed state.

In some embodiments the physical subject is a honeybee dance and potential states of the honeybee dance are a right turn state, a left turn state, and a waggle state.

In some embodiments the plurality of multivariate signals are nonlinear and non-stationary signals.

In some embodiments the statistical characteristics of the plurality of multivariate signals include maximum and minimum values of the plurality of multivariate signals.

In some embodiments the statistical characteristics of the plurality of multivariate signals are monitored at a reduced rate relative to the sampling rate.

In some embodiments the respective plurality of state change artifact signals are eye opening or eye closing artifact signals.

In some embodiments the features are extracted from the one or more of the plurality of intrinsic mode functions over a reduced time interval relative to the critical time interval.

In some embodiments the features are extracted from one or more of the plurality of intrinsic mode functions over a reduced time interval relative to the critical time interval, using a common spatial pattern method.

Other aspects of the invention will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
FIG. 1 shows an Emotive EPOC neuroheadset and its channel locations.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions. Articles "a" and "an" are used herein to refer to one or to more than one (at least one) of the grammatical object of the article. By way of example, "an element" means at least one element and can include more than one element. Unless otherwise defined, all technical terms used herein have the same meaning as commonly understood by one of ordinary skill in the art to which this disclosure belongs.

Embodiments are described herein with reference to flowchart illustrations and/or block diagrams and/or figures. The flowchart, block diagrams and other illustrations in the present disclosure illustrate the architecture, functionality, and operation of possible implementations of systems, methods, computer program products (non-transitory computer-readable medium storing instructions executable one electronic processors, such as a microprocessor, to perform a set of functions), and the like according to various embodiments of the present invention. In this regard, each block in the flowchart or block diagrams, or accompanying figures herein may represent a module, segment, or portion of instructions, which comprises one or more executable instructions for implementing the specified logical function(s). In some alternative implementations, the functions noted in the block or figures may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration and/or figures and combinations of blocks in the block diagrams and/or flowchart illustration and/or figures can be implemented by special purpose hardware-based systems that perform the specified functions or acts or carry out combinations of special purpose hardware and computer instructions.

A fast analytic method has been developed to identify random eye state change in real-time using brain signals. Broadly speaking, a mixture of analytic process control, signal processing, and machine learning analytics are utilized. While others may use the same dataset, as disclosed herein, their classification algorithms perform unnecessary, time consuming, and energy inefficient computations. The present disclosed approach is different because it takes the random nature of the eye state change into account through a control process. Then, it utilizes state of the art machine learning analytics to classify the state of the eye upon detection of a potential change. This process provides a valuable improvement in comparison to slow, computationally analytic difficulties in the published literature.

The disclosed analytics utilized in modeling multivariate brain signals can be adopted to analyze other biomedical signals and time series data in real-time. The process control monitors the input for potential change. Upon detection of a possible change, fully data-driven analytic steps are used to extract discriminant features from the segmented input signal. Then, machine learning analytics such as Logistic Regression, Artificial Neural Network (ANN), and Support Vector machine (SVM) are employed to verify the change.

The analytic findings have been employed in detecting the three different dance moves that honey bees perform to communicate the location of a food source. The results are significantly better than other methods in the literature such as Switching Linear Dynamic System (SLDS) proposed by Oh et al., signal segmentation using a first-order Auto-Regressive AR(1) proposed by Xuan and Murphy, and sticky Hidden Markov Model (HMM) with Hierarchical Dirichlet processes (HDP) and switching Vector Autoregressive (VAR) proposed by Fox.

To shed light on the importance of the results, decoding a honeybee waggle dance aids in commercial crop pollination and could be followed by other larger studies. An obvious example is the California almond crop, for which approximately one million bee colonies are rented each year during spring bloom and which according to an FAO report in 2015 had an annual value of $5.7 billion.

Other applications of this analytic method and system include:

Real-time epileptic seizure prediction using brain signals where early detection and prediction might be able to abort seizures through targeted therapies or could prevent accidents and limit injury.

Monitoring Market price for a significant change of patterns, then employing machine learning for making decisions upon detecting potential change.

Detecting Change of Motion through video or biomedical signals achievable by monitoring for a possible change and then using machine learning when a possible change happens.

Autonomous cars to continue a former pattern unless a significant change in the conditions has taken place.

The monitoring-action process significantly improves the processing time of classifying signals. The processing time is an issue with machine learning analytics.

The average human brain is estimated to have about 86 billion neurons making up a complex integrated information processing and control system that regulates all the conscious and unconscious daily decisions. The ability to recognize biological motion perceptions and physiological changes through brain signals has been studied for many reasons especially medical diagnosis and Brain-Computer Interface (BCI). Electroencephalogram (EEG) provides a non-invasive tool to record the brain's electrical potential along the scalp at multiple locations over the scalp. It measures voltage fluctuations resulting from ionic current flows within the neurons of the brain. Discriminating between the open and closed state of the eyes using EEG signals in real-life situations is a challenging research goal not only crucial to medical care but also significant to several daily life tasks.

The significance of eyes state identification using EEG signals is shown through related studies in scientific literatures. Some of the applications include automated classification of sleep-waking states in infants and hospitalized patients, stress feature identification, human-computer interface design, alertness of pilots especially fighter jet pilots, and detection of driving drowsiness where it estimated to be responsible for at least 72,000 crashes, 44,000 injuries, and 800 deaths in 2013. Various methods have been used in literature to achieve higher classification accuracy; among them are embedded hidden Markov models, time series classification, pattern recognition, and machine learning methods. In this research innovation a fully data-driven method which can handle non-linear, non-stationary, and multivariate signals is fused with spatial filtering and common machine learning classification methods to achieve a fast real-time classification analytics with a very high prediction accuracy.

Aside from neural activities, EEG captures potential fluctuations of non-neural origins such as technical and biological artifacts. DC noise, power line, improper placements, and high impedance of EEG electrodes create technical artifacts. Eye movements and blinks, muscle contractions, and heart activity are among the biological artifacts that a person creates. Eye blink artifacts are generated by the movement of the eyelid along the cornea. By friction between lid and cornea, this movement results in charge separation, with a dominant dipolar charge distribution, and the dipole moment pointing in up-down direction. In the EEG, this effect is recorded as a positive peak that lasts a few tenths of a second, is most visible in the frontopolar region, but propagating to all the electrodes of the montage, becoming weaker with distance from the frontal part. The frequency bands that are more affected by this artifact are $\delta$ (0.5-4.0 Hz) and $\theta$ (4-8 Hz), with the main portion of energy below 5 Hz. Among neural activities, a band signals that are associated with wakefulness, closing the eyes, effortless alertness, and creativity are triggered normally in the posterior half of the brain in the frequency range of 8-13 Hz.

FIG. 1 illustrates an Emotiv EPOC neuroheadset and its channel locations. The dataset used in this study is publicly available via UCI Machine Learning Repository. It was recorded by an Emotiv EPOC headset that records brain signals with 128 Hz sampling frequency in 14 locations on the scalp. Using this dataset, Rösler and Suendermann applied various instance based classification methods and achieved 97.3% accuracy using R-Star algorithm. But their algorithm took at least 2 hours to train and 20 minutes to predict the state of the eye for a new instance. In another study, Wang et al. have extracted standard deviation and average of channels as new features and used Incremental Attribute Learning to achieve an accuracy of 76.6% for eye state classification. They did not report the running time of their procedure. In a more recent study, Sabanci and Koklu have employed k-Nearest Neighbors and multilayer perception neural networks algorithm to classify the eye state. Their highest achieved success rate was 84.05% by three nearest neighbors' method yet the runtime was not reported. Considering the data recording speed, these three studies follow slow and computationally intensive instance based algorithms. Besides, the nature of the experiment in which the eye state randomly changes in time, does not require going through classification procedures for every instance.

In the embodiments discussed herein, cross-channels maximum and minimum were employed to monitor recording instances in real time. Upon detection of a possible change, Multivariate Empirical Mode Decomposition analytics are applied to the last two seconds of the signal to extract narrow-band Intrinsic Mode Functions. Then, selected Intrinsic Mode Functions are passed through Common Spatial Pattern to extract relevant features. Finally, features are fed into classification analytics to decide whether a change in the eye state has occurred. Furthermore, a second procedure uses analytical statistical features from Intrinsic Mode Functions which is then fed directly to the classification analytics. Both procedures take less than two seconds to predict a change in the eye state and could be employed in real-time eye state detectors.

The EEG eye state corpus from UCI Machine Learning Repository created by Frank and Asuncion in 2010 is utilized. The dataset was recorded using Emotiv EPOC headset in an experiment conducted in 2013 by Rösler and Suendermann from Baden-Wuerttemberg Cooperative State University (DHBW), Germany. During the experiment which was conducted in two sessions of one to two minutes each, a participant closed/opened his/her eyes at will. Brain signals recorded from 14 different locations on the scalp namely AF3, AF4, F3, F4, F7, F8, FCS, FC6, T7, T8, P7, P8, O1, and O2 at 128 Hz sampling frequency. The eye state added to the data after investigating a camera feed which was focused on the eyes. After dumping the first few seconds of the recording, only 117 seconds of the signals, a total of 14,980 instances in 15 attributes, were made available online at UCI machine learning repository.

The performance of the EPOC headset in this specific task has been compared to medical grade BrainAmp Standard device by Rösler et al. and the difference was insignificant. In comparison to the BrainAmp Standard, the EPOC headset has a significantly lower price, a higher usability due to its wireless connection, and a faster and easier setup which emphasizes its advantageous applicability.

Figure 2:
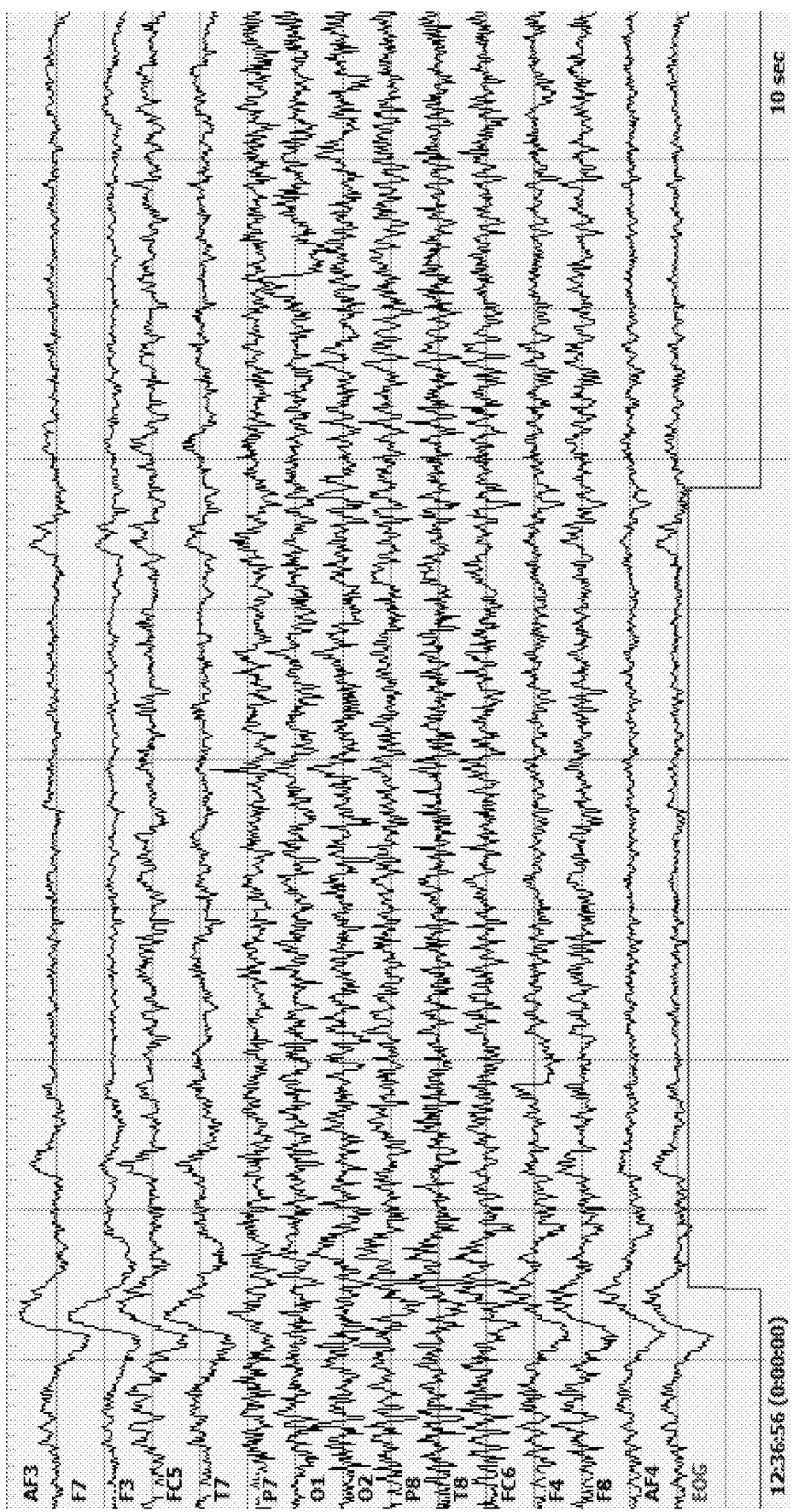
FIG. 2 shows the first 10 seconds of a filtered signal for all channels plus eye state.

Upon visual inspection of the dataset, instances 899, 10387, 11510, and 13180 were removed from the data since they tackled an outlier in some of the channels. A high-pass Butterworth filter of 0.5 Hz is then used to remove the DC offset. FIG. 2 shows the first 10 seconds of the normalized signal which includes closing eye (1) and opening eye (0) events. The rhythmic activity of Event-Related Synchronization (ERS) and Event-Related De-synchronization (ERD) is detectable by eye right before changing eye state in most of the channels. The cleaned signal was shown by $X^{ch \times t}$ hereinafter where ch=14 is the number of channels and t=14,976 is the time instances.

Figure 3:
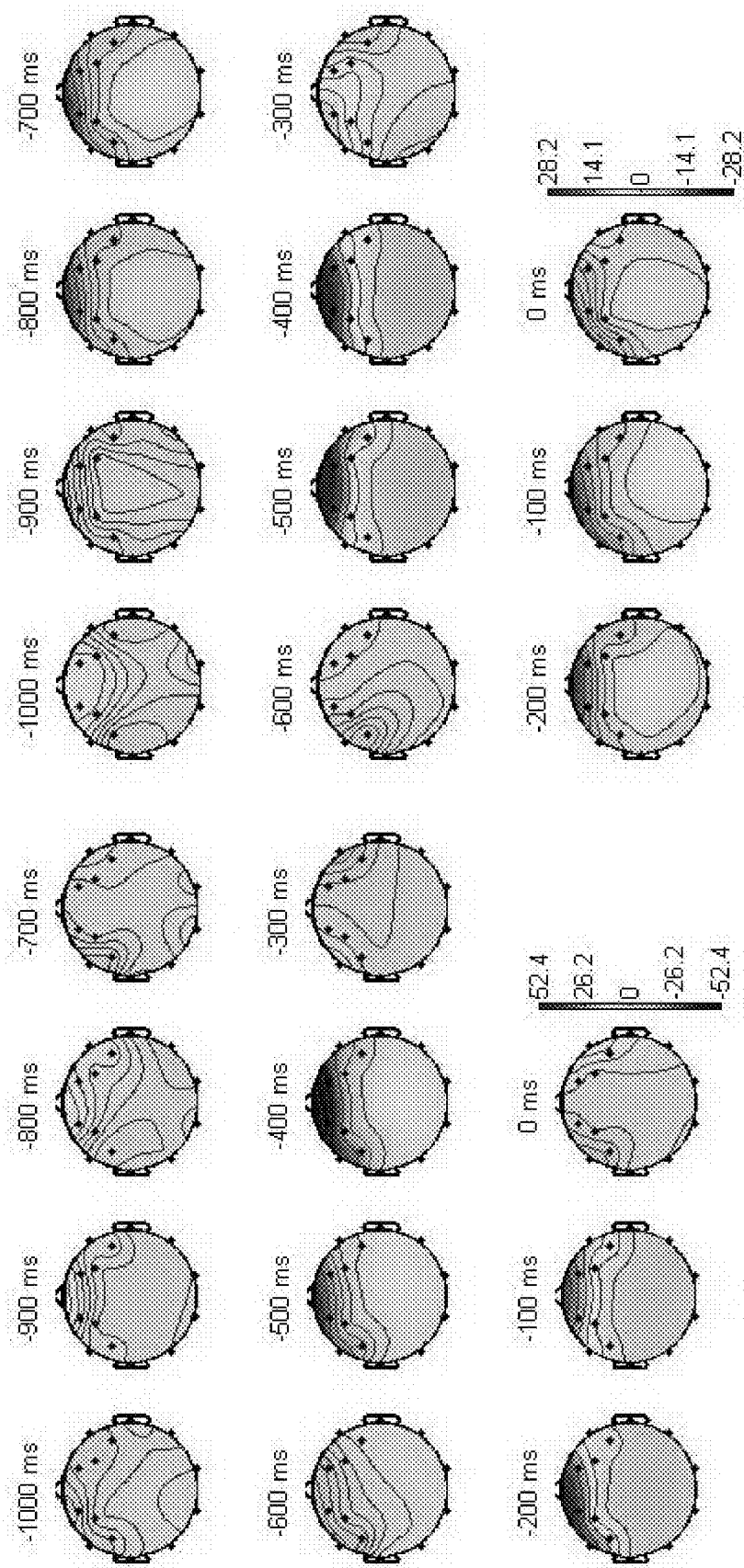
FIG. 3 shows scalp maps for average epochs: (a) before closing eyes, and (b) before opening eyes.

A total of 12 closed eyes and 11 open eyes intervals with various lengths are available in the dataset. After cutting these 23 intervals into one-second epochs right before change of the eye state, the average amplitude of epochs for each eye state were computed and localized using EEGLAB. Some of the intervals were not disjoint. FIG. 3 shows the scalp map of the brain activity for the average amplitude over epochs. ERS/ERD is noticeable especially in the frontal part of the head where channel AF3 and AF4 are located. This charge is due to muscle activity.

Figure 4:
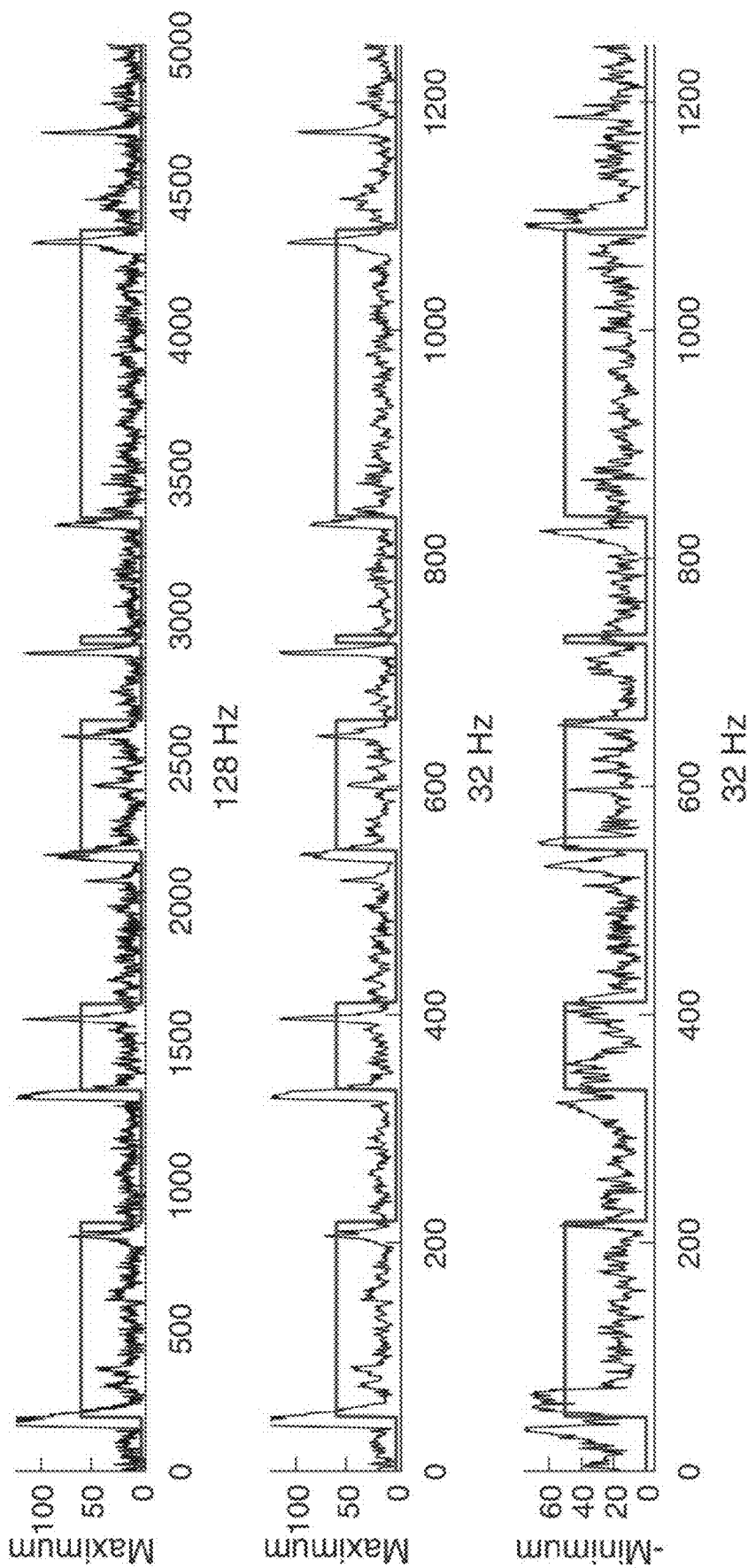
FIG. 4 shows a cross-channel maximum at 128 Hz frequency, a maximum at 32 Hz frequency, and a minimum at 32 Hz frequency.

Considering the sampling frequency of 128 Hz, each second 128 instances are recorded in 14 channels. Running instance-based classification algorithms is slow and computationally intensive. Instead, we propose monitoring the instances in real time until a possible change of the eye state is observed. After going through some statistical characteristics of the channels such as variance, average, minimum, maximum, range and midrange, the maximum and minimum computed across channels defined by $$\max(t) = {}_{ch}^{max}(X^{ch \times t}) \quad (1)$$

and $$\min(t) = {}_{ch}^{min}(X^{ch \times t}) \quad (2)$$

were selected as monitoring functions. This selection is compatible with the results of FIG. 3 where the signals amplitude decreases then increases significantly right before closing eyes (a) and it increases then drops significantly right before opening eyes (b). FIG. 4 illustrates that the eye state change happens in synch with significant increase of both eq. (1) and eq. (2). This increase is more notable in changing the eye state from open to closed. There are also a few noticeable peaks in monitoring functions when the eyes are open which are probably due to unregistered blinking.

There is no need to compute the monitoring eq. (1) and eq. (2) for every instance as every four instances are good enough to detect a change of eye state efficiently. That is, a 32 Hz input signal for the monitoring performs well. This reduces the computational cost for the penalty of losing the exact instance the change happens. However, considering the speed of recording instances and the nature of the experiment, the gain is worth the cost.

The eye state change time is random since the participant closes/opens the eyes without further notice. The change of eye state affects the brain signals due to eye muscle movement artefact and alpha band signal activity. The monitoring max(t) and min(t) given by eq. (1) and eq. (2) computed at 32 Hz can pick up this change, thus applying a threshold for these two functions is an efficient way to detect possible change of eye state.

The utilized closing eye indicator was dropping the min(t) less than −45 μv and then rising above 55 μv within 7-9 instances. This indicator did not pick up three blinking epochs that originally lasted for 28, 40, and 52 instances and signaled one false alarm. The utilized opening eye indicator was raising the max(t) above 45 μv and then dropping under −40 μv within 5-9 instances. This indicator did detect all the opening eye epochs. The thresholds have been assigned by experimenting. Although the monitoring results did not match exactly with the changing class label times, they provided a close range of (−12, 12) instances from the actual class labels.

Multivariate Empirical Mode Decomposition (MEMD) is a data driven method that localizes time-frequency information in multivariate, non-stationary, low signal-to-noise ratio, and closely spaced frequency bands EEG signals. The open source MATLAB codes that are available through have been used in this dissertation to decompose the filtered signals into narrow-band components. Empirical Mode Decomposition (EMD) introduced by Huang et al., decomposes a one-dimensional input signal, x(t), into a finite set of Intrinsic Mode Functions (IMF), $c_i(t)$, i=1, . . . , M, that is, $$x(t) = \sum_{i=1}^{M} c_i(t) + d(t), \quad (3)$$

by using the following analytic procedure:
1. Find the locations of all the extrema of x(t).
2. Interpolate between all the minima (respectively maxima) to obtain the lower (upper) signal envelop $e_{min}(t)$ (respectively $e_{max}(t)$).
3. Compute the local mean $m(t)=(e_{min}(t)+e_{max}(t))/2$.
4. Subtract the mean from the signal to obtain the "oscillatory mode" s(t)=x(t)−m(t).
5. If s(t) obeys the stopping criteria, then define c(t)=s(t) as an IMF, otherwise set x(t)=s(t) and repeat the process from step 1.

Once the first IMF is obtained, the same procedure is applied iteratively to the residual d(t)=x(t)−c(t) to extract the remaining IMFs. The stopping criteria require that the number of exterma and zero crossings differ at most by one.

Every IMF is a narrow-band signal reflecting a different temporal scale intrinsic to the input signal. The IMFs are used to obtain a localized time-frequency spectrogram using Hilbert transform. However, analyses of EEG signals which are recorded simultaneously by channels require multivariate techniques that capture the cross-channel interdependence. Multivariate EMD, uses a vector-valued form to simultaneously decompose a p-variate signal x(t) to $$x(t) = \sum_{i=1}^{M} c_i(t) + d(t), \quad (4)$$

where $c_i(t)$, i=1, . . . , M, are the p-variate IMFs containing scale-aligned intrinsic joint rotational modes and d(t) is the residue. This is accomplished via the following analytic procedure. Consider the sequence of p-variate signal $\{x(t)\}_{t=1}^{T}$, and suppose $S_{\theta_k}=\{S_k^1, \ldots, S_k^p\}$ denote a set of direction vectors along the directions given by angles $\theta_k=\{\theta_k^1, \ldots, \theta_k^{(p-1)}\}$ on a (p−1) sphere. Then,
1. Choose a pointset for sampling on a (p−1) sphere, let $\theta_k=\{\theta_k^1, \ldots, \theta_k^{(p-1)}\}$ be the angles of the direction vectors.
2. Calculate the projections $\{p_{\theta_k}(t)\}_{t=1}^{T}$ of the input signal $\{x(t)\}_{t=1}^{T}$ along the direction vector $S_{\theta_k}$, for k=1, . . . , K (the whole set of direction vectors) giving the set of projections $\{p_{\theta_k}(t)\}_{k=1}^{K}$.
3. Find the time instants $\{t_{\theta_k}^i\}_{k=1}^{K}$ corresponding to the maxima of the set projected signals $\{p_{\theta_k}(t)\}_{k=1}^{K}$.
4. Interpolate $[t_{\theta_k}^i, x(t_{\theta_k}^i)]$ to obtain the multivariate envelope curves $\{e_{\theta_k}(t)\}_{k=1}^{K}$.
5. Calculate mean of the K multidimensional envelope curves $$m(t) = \frac{1}{K} \sum_{k=1}^{K} e_{\theta_k}(t).$$

6. Extract the detail c(t)=x(t)−m(t). If c(t) fulfills the stopping criterion for a multivariate IMF, apply the above procedure to x(t)−c(t), otherwise apply it for c(t).

Figure 5:
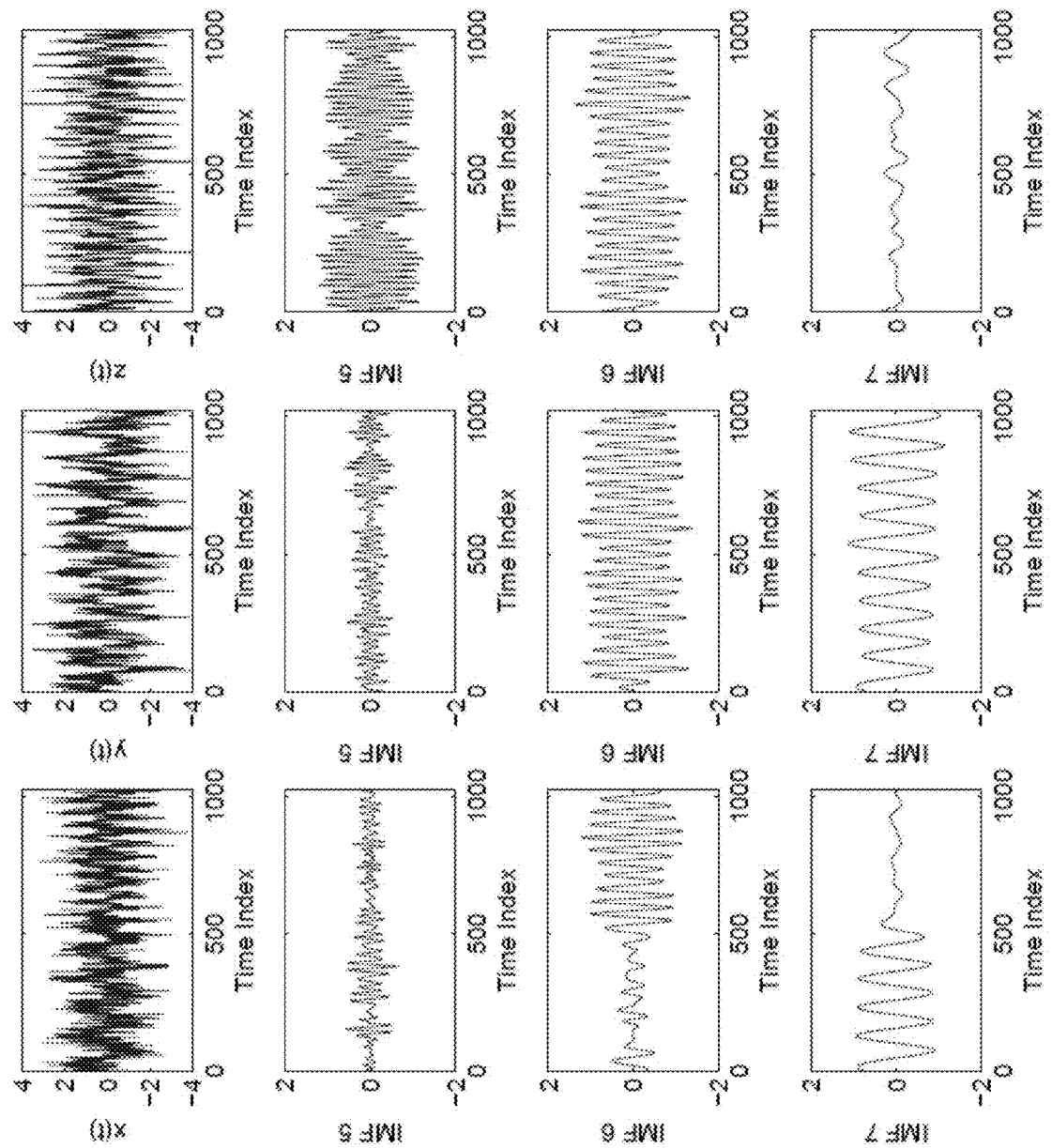
FIG. 5 shows intrinsic mode functions (IMFs) 5-7 of a three dimensional signal (xt, yt, zt) derived using multivariate empirical mode decomposition (MEMD).

The analytic procedure is fully data-driven with no prior assumptions which give it an upper hand for analyzing nonlinear and non-stationary phenomena such as EEG signals. See FIG. 5 for an example that shows how MEMD decomposes a three dimensional signal $(x_t, y_t, z_t)$ into a collection of narrow-band frequency signals. The signal is given by $$x_t = \begin{cases} \sin(2\pi f_1 t + WN, & t=1, \ldots 512, \\ \sin(2\pi f_2 t + WN, & t=513, \ldots, 1024, \end{cases}$$

$$y_t = \sin(2\pi f_1 t) + \sin(2\pi f_2 t) + WN, \quad t=1, \ldots, 1024,$$

$$z_t = \sin(2\pi f_2 t) + \sin(2\pi f_3 t) + WN, \quad t=1, \ldots, 1024,$$

where $f_1=5/f_s$, $f_2=11/f_s$, $f_3=23/f_s$, $f_s=128$ and WN represents white noise.

Common Spatial Pattern (CSP) which is widely used in BCI applications creates spatial features that maximize the variance of the signals in one class while minimizing the variance of signals in the other class. This leads to creating discriminant features to classify two populations of EEG signals. It has been used herein to design features to classify open/closed eye states. The CSP analytic driven algorithm is described as follows. Suppose $S^{(c)} \in \mathbb{R}^{Ch \times Ch}$ and) $S^{(o)} \in \mathbb{R}^{Ch \times Ch}$ are the pooled estimates of the covariance matrices of the band-pass filtered EEG signal $X^{ch \times t}$ in the two conditions, i.e. closed and open eyes, given by $$S^{(j)} = \frac{1}{|I_j|} \sum_{i \in I_j} X_i^{chxt}(X_i^{chxt})^T, \quad j \in \{c, o\}, \quad (5)$$

where $I_j$ is the set of indices corresponding to trials belonging to each condition and |I| denotes the size of the set I. The CSP analysis seeks to find a matrix $W \in \mathbb{R}^{Ch \times Ch}$ and diagonal matrices $\Lambda^{(c)}$ and $\Lambda^{(o)}$, such that, $$W^T S^{(c)} W = \Lambda^{(c)}, \ W^T S^{(o)} W = \Lambda^{(o)}, \text{ and } \Lambda^{(c)} + \Lambda^{(o)} = I. \quad (6)$$

This is accomplished by solving a generalized eigenvalue problem. Having W, it allows projecting the EEG signals as $$Z = W^T X. \quad (7)$$

For discriminating between two tasks, the variances of the spatially filtered signals by eq. (7) are used as feature. The row vectors $z_p$ from Z that maximize the difference in the variance between two groups are associated with the largest eigenvalues in $\Lambda^{(c)}$ and $\Lambda^{(o)}$. These signals are contained in them first (p=1, . . . , m) and last (p=ch−m+1, . . . , ch) rows of Z in eq. (7). The spatial features can then be obtained as $$f_p = \frac{\text{var}(z_p)}{\sum_{\substack{i=1,\ldots,m \\ i=ch-m+1,\ldots,ch}} \text{var}(z_i)}, \quad (8)$$

where var(.) denotes the variance and $f_p \in \mathbb{R}$ is a real number. This means that by using only the first and last two rows of Z, four numbers are extracted as representatives of 2 s long signals recorded in 14 locations. Thus, CSP provides a huge dimension reduction.

Figure 6:
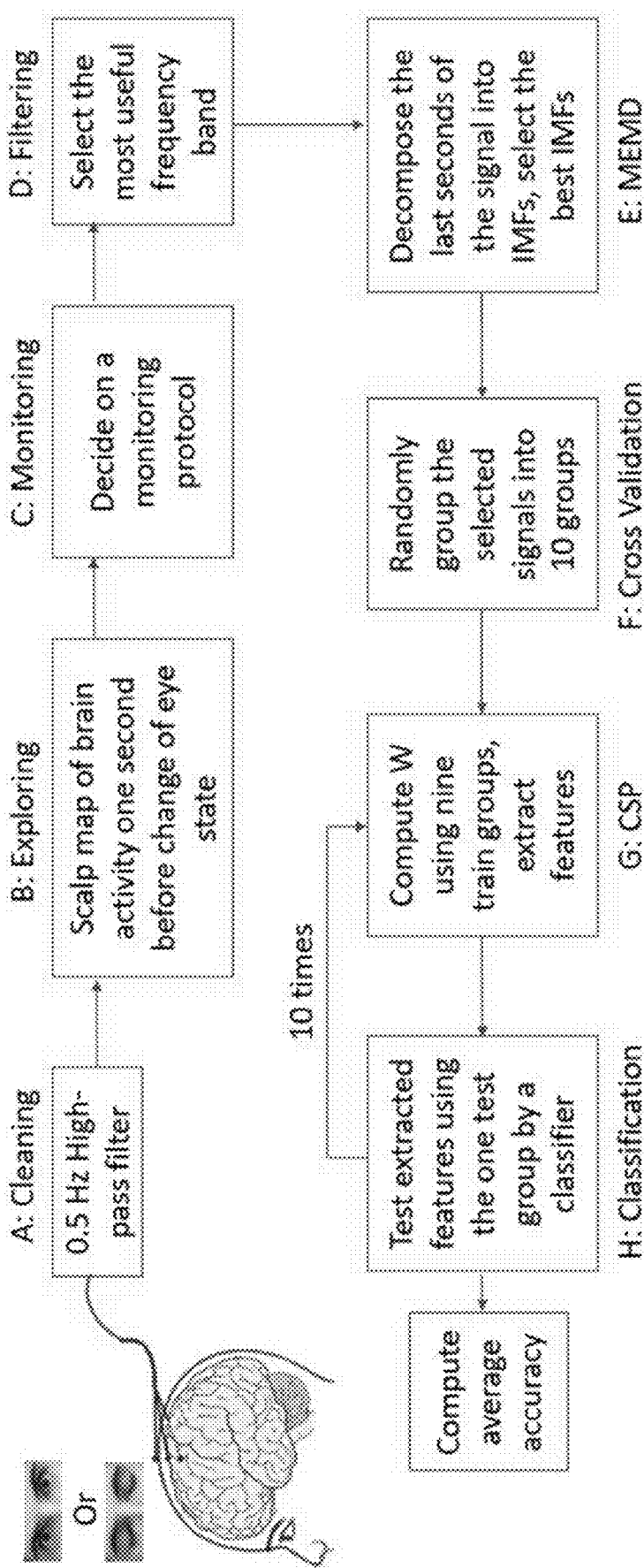
FIG. 6 illustrates an overall process of developing an accurate changing eye state detector.

Referring to FIG. 6, the overall process of developing the accurate changing eye detector is illustrated. The process starts with cleaning the input signal by passing it through a 0.5 Hz high-pass filter (A). Continue with exploratory analysis to compare brain activity right before change of eye state (B). Then, monitoring functions and protocols are set to watch the input and alert for potential eye state change (C). After an alert from monitoring functions, a frequency band that carries the right information for our goal is selected (D). The selected frequency band signal is then decomposed into narrow-band IMFs using MEMD and the most discriminative IMFs are selected to proceed (E). The selected IMFs are then grouped randomly into ten exclusive groups in cross-validation step (F). Nine groups are used to estimate spatial filter matrix W using CSP. Then, W is used on all the train and test signals to extract features (G). Using the same cross-validation groups, the nine training groups are used to train a classifier and the one test group is used to test its performance (H). The average accuracy of the ten test groups performances is then recorded. Note that this was a back and forth process and the final proposed analytics is decided by experimenting with various options in each step.

The eye state change time is random since the participant closes/opens the eyes without further note. The change of eye state affects the brain signals due to eye muscle movement artefact and alpha band signal activity. The monitoring max(t) and min(t) given by eq. (1) and eq. (2) computed at 32 Hz can pick up this change, thus applying a threshold for these two functions is an efficient way to detect possible change of eye state.

The utilized closing eye indicator was dropping the min (t)←−45 and then rising the max(t) above 55 within 7-9 instances. This indicator did not pick up three blinking epochs that originally lasted for 28, 40, and 52 instances and signaled one false alarm. The utilized opening eye indicator was rising the max(t) above 45 and then dropping the min(t) under −40 within 5-9 instances. This indicator did detect all the opening eye epochs. The thresholds have been assigned by trial and error. Although the monitoring results did not match exactly with the changing class label times, they provided a close range of (−12, 12) instances from the actual class labels.

Figure 7:
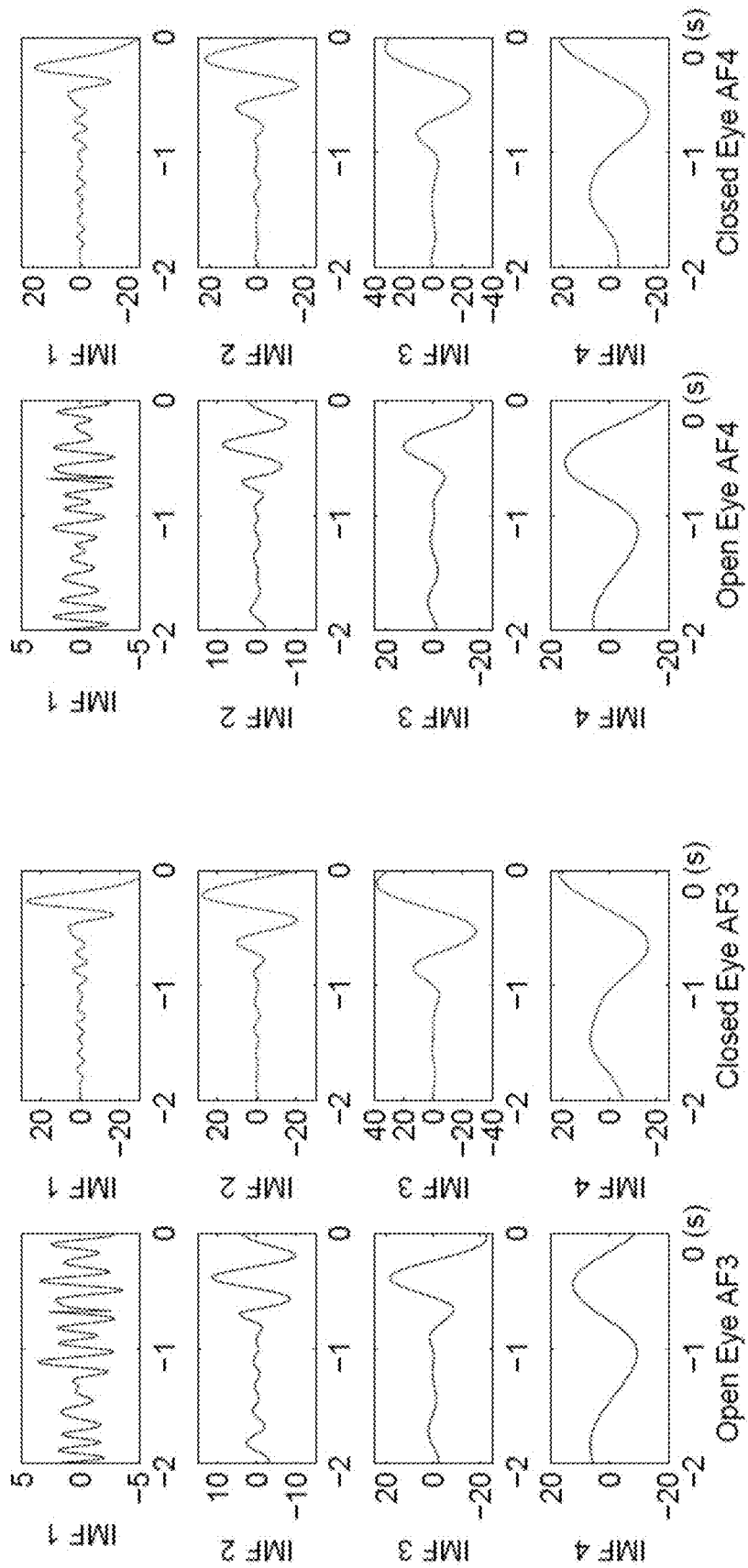
FIG. 7 shows the first four IMFs of open/closed eye state averaged epochs after a 0.5-8 Hz filter.

The cleaned signal $X^{ch \times t}$ is first passed through a low-pass filter of 8 Hz to include only the $\delta$ and $\theta$ band signals. The signal is then divided into 17 intervals of variable sizes based on the monitoring results. The average over all the epochs for each eye state has been computed for the last two seconds of the signals before changing eye state and the average passed through MEMD. If a signal was shorter than two seconds, the available instances have been used in the average. FIG. 7 shows the first four IMFs of the open and closed eye state for channels AF3 and AF4.

Obviously, there is a change in behavior of the IMF signals right before the change of the eyes state. Typically, the closed eye has more energy especially when getting close to the event of changing the eye state. The signals for channel AF3 have higher amplitude. Similar patterns observed in IMF signals of other channels and the signal strength decayed by moving further from the frontal part of the head.

Figure 8:
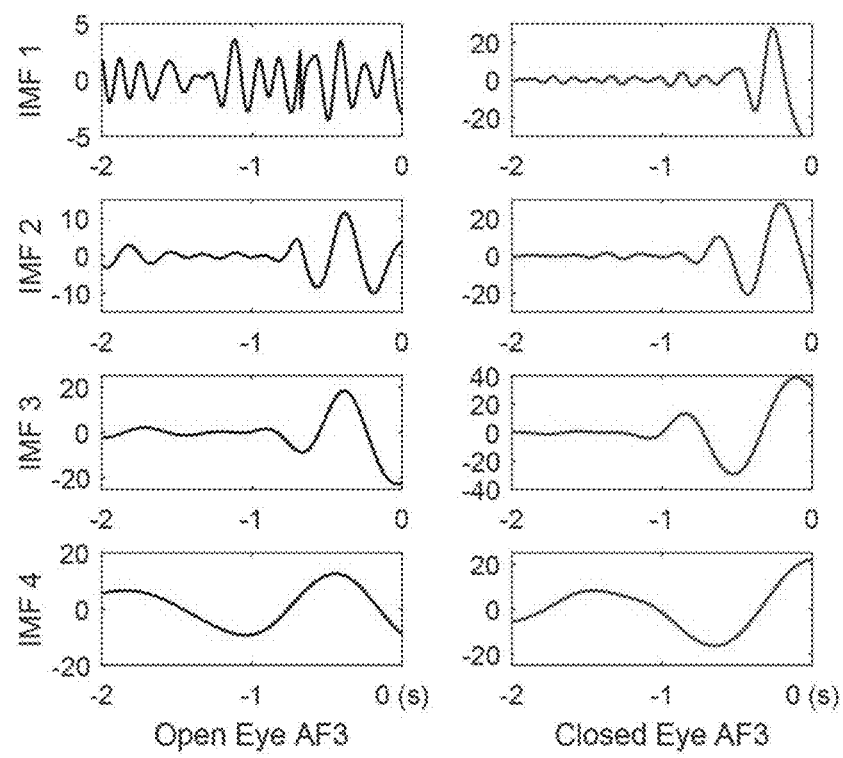
FIG. 8 shows the first four IMSs of open/closed eye state averaged epochs after an 8-13 Hz filter.
Figure 8:
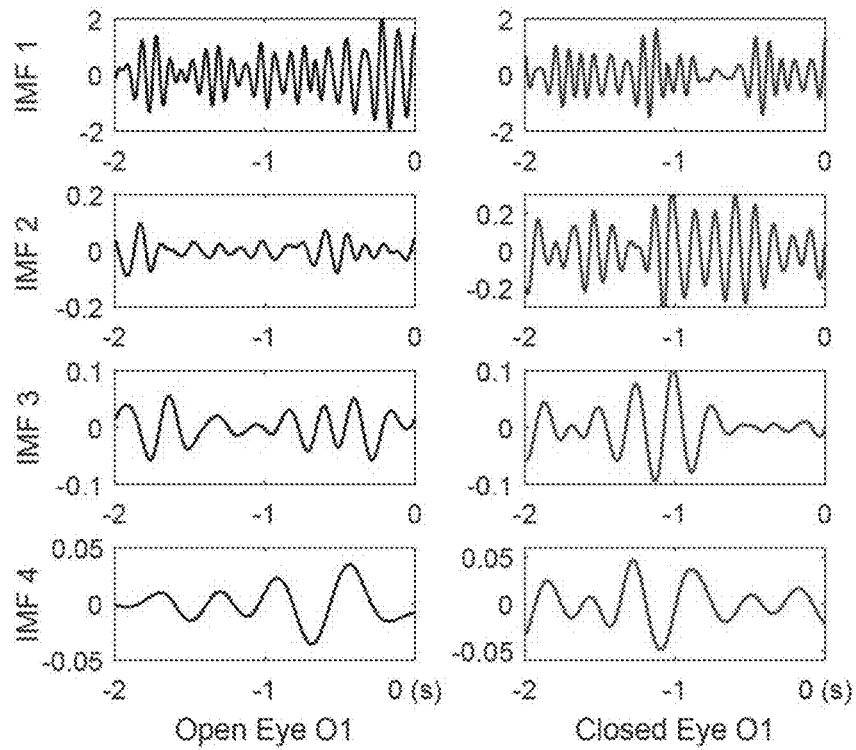

The process then repeated using a band-pass filter of 8-13 Hz to investigate the effect of $\alpha$ band frequency. FIG. 8 shows the first four IMFs of the open and closed eye state for channels O1 and O2. The IMF signals were stronger in these two channels and decayed by moving further away from posterior part of the head. The two channels have roughly the same patterns and characteristics such as power spectral, variance, and range. Notice the amplitude of signals which is a lot less than signals in FIG. 7 but the frequencies are higher. The difference between the two states is detectable but the numerical values tested for features such as power spectrum, variance, maximum, and range is not significantly different. Considering FIG. 7 and statistical characteristics of IMF signals in the two eye state, only band-pass filter of 0.5-8 Hz which is related to the eyes muscle activity is used for further analysis.

Two different feature extraction methods were developed and classification procedures were performed on each of them separately. In the first method, a Common Spatial Pattern which is discussed in chapter 1 is used. In the second method, statistical properties of signals in the two eye state that provide better discriminant features are employed to extract features. The results of the two methods are then compared.

Features relevant to the two eye state were extracted using CSP algorithm. CSP filters should be calculated from training data and the resulting filters need then to be applied to the test set. For this purpose and to evaluate the efficiency of the predictive analytic model, 10-fold cross-validation has been used. That is, the band-pass filtered (0.5-8 Hz) data including 9 open eye and 8 closed eye epochs has been divided into ten subsets where each time four subsets used for training the classifier and one for testing the performance.

The test and training signals first passed though MEMD to extract oscillatory IMFs. The first IMF of the training signals which provided the best discriminant statistics is then used to compute the spatial filters W using CSP. The first two and last two spatial filters then applied to both the test and training IMFs as described in eq. (7) and their $f_p$ features were calculated using eq. (8). Finally, three classification methods have been used to assess the accuracy of the analytic model. Table 1 below, provides average results of the five-fold classification using logistic regression, artificial neural networks, and support vector machine classifiers.

TABLE 1

Classification Results

| Features | Logistic Regression | | ANN 4 × 4 × 2 | | SVM Gaussian Kernel σ = 0.5 | |
| --- | --- | --- | --- | --- | --- | --- |
| | Accuracy | F-Score | Accuracy | F-Score | Accuracy | F-Score |
| IMF1:$f_2,f_3$ IMF2:$f_1,f_3$ | 0.834 | 0.854 | 0.834 | 0.802 | 0.834 | 0.854 |
| IMF1:$f_1,f_3$ IMF2:$f_1,f_4$ | 0.834 | 0.828 | 0.834 | 0.828 | 0.766 | 0.820 |
| IMF1:$f_1,f_3$ IMF2:$f_1,f_2$ | 0.784 | 0.828 | 0.766 | 0.750 | 0.716 | 0.794 |
| IMF1:$f_2,f_3$ IMF2:$f_1,f_4$ | 0.768 | 0.788 | 0.766 | 0.668 | 0.784 | 0.728 |

The set of features were selected upon visual inspection of the features' matrix scatter plots. The combination of four features, two from IMF1 and two from IMF2, provided higher accuracy than features from one IMF alone. Features from IMF3 were not used because of their low test accuracy. The best classification performance for Simple Logistic Regression, Artificial Neural Network (4×4×2), and Support Vector Machine with Gaussian Kernel ($\sigma$=0.5) classifiers achieved by utilizing features $f_2$, $f_3$ from IMF1 and $f_1$, $f_3$ from IMF2, accuracy of 83.4%. The average F-score which is the ratio of precision to recall was 0.854 for both Simple Logistic Regression and Artificial Neural Network, and was 0.802 for Support Vector Machine. The default value of 0.5 has been used for Gaussian kernel standard deviation in SVM method since the training size was not large enough to perform model parameters' estimation.

Figure 9:
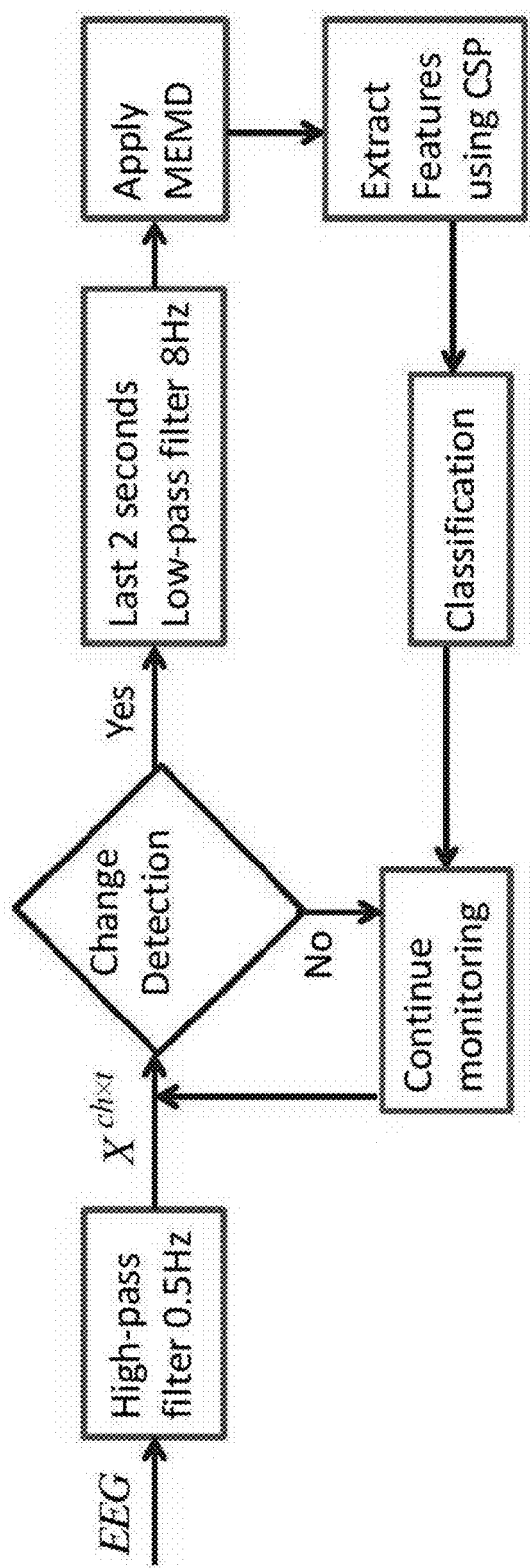
FIG. 9 shows a prediction process using common spatial pattern (CSP).

Real-time prediction follows the procedure shown in FIG. 9. First, the signal is passed through a high-pass Butterworth filter of 0.5 Hz to remove the DC offset. The cleaned signal is monitored in real time by min(t) and max(t) computed at 32 Hz. Upon detection of a change in the eye state, the last two seconds of the 128 Hz signal is passed through a low-pass filter of 8 Hz to include only the eye movement artifact. The filtered signal is then passed through Multivariate Empirical Mode Decomposition and four features ($f_2$, $f_3$ from IMF1, $f_1$, $f_3$ from IMF2) are extracted using CSP method. The features are then fed to a logistic regression classifier to predict the eye state. The monitoring then continues. The procedure needs calibration to estimate the spatial filters W before applying.

Investigating FIG. 7, a change in variance of the IMF signals is obvious right before change of the eyes state. In addition, looking at the range of the y-axis, the first three IMFs clearly show a higher amplitude in the close than open eye states. This motivates using the variance and maximum of the first three IMFs as discriminant features. The similarity between the IMFs of the AF3 and AF4 channels suggests averaging their computed features for higher reliability. Therefore, variance and maximum of the last one second of the first three IMFs were computed for channels AF3 and AF4 then averaged and marked as potential features. These features presented in Table 2 provide the most discriminant values between the two eye states, especially Max1 and Var2 which are the maximum of first and variance of the second IMF, respectively.

TABLE 2

Extracted Features from relevant IMF number

| Max1 | Max2 | Max3 | Var1 | Var2 | Var3 | Class |
|---|---|---|---|---|---|---|
| 13.03 | 34.09 | 34.60 | 31.51 | 293.56 | 356.22 | C |
| 13.18 | 46.47 | 36.97 | 31.88 | 478.27 | 451.94 | C |
| 11.22 | 13.68 | 45.59 | 28.85 | 59.08 | 709.03 | C |
| 10.92 | 28.40 | 34.86 | 20.31 | 208.63 | 410.00 | C |
| 13.98 | 21.20 | 46.59 | 44.21 | 168.20 | 773.56 | C |
| 8.99 | 27.01 | 35.72 | 17.83 | 187.53 | 459.14 | C |
| 17.96 | 26.30 | 23.06 | 44.87 | 179.57 | 173.45 | C |
| 7.33 | 39.57 | 59.16 | 11.97 | 413.06 | 885.72 | C |
| 28.30 | 44.56 | 26.34 | 140.33 | 481.84 | 170.15 | C |
| 10.74 | 11.28 | 20.21 | 17.47 | 31.90 | 164.18 | O |
| 5.02 | 28.50 | 34.81 | 5.02 | 173.97 | 439.28 | O |
| 19.02 | 7.93 | 24.27 | 62.11 | 18.97 | 259.55 | O |
| 8.31 | 23.89 | 37.62 | 12.71 | 127.14 | 671.07 | O |
| 12.10 | 13.23 | 7.12 | 27.94 | 37.49 | 19.02 | O |
| 9.96 | 18.06 | 20.78 | 20.58 | 81.80 | 204.45 | O |
| 5.49 | 3.55 | 3.38 | 6.61 | 3.95 | 4.18 | O |
| 10.96 | 8.24 | 15.72 | 19.39 | 21.15 | 83.34 | O |

To evaluate the efficiency of the predictive analytic model, five-fold cross-validation has been used. That is, the data set including 9 open eye and 8 closed eye epochs has been divided into five subsets where each time four subsets used for training the classifier and one for testing the performance. Table 3 provides average results of the five-fold classification using Logistic Regression, Artificial Neural Networks, and Support Vector Machine classifiers.

Simple Logistic Regression classified the two eye states with an accuracy of 88.2% using only two features, Max1 and Max2. The average F-score which is the ratio of precision to recall was 0.882. Accuracy of Artificial Neural Network classifier with three hidden layers was 82.4% with F-score of 0.824 for the same features. Using Max1 and Var2 features ANN achieved a higher accuracy, 88.2%. Support Vector Machine classifier's average accuracy was 70.1% for the two sets of features. Linear Kernel has been used for SVM classifier. These performances could be improved by further training the classifiers with more samples. More training examples also provide enough data to utilize regularized logistic regression which can improve the accuracy by adjusting a regularization factor. In addition to the reported accuracies that are based on cross-validation of 17 eye state changes, the instance based accuracies were computed that count the percentage of correct predicted instances. These accuracies were 0.877 (Max1, Max2) and 0.786 (Max1, Var2) for Logistic Regression and 0.815 (Max1, Max2) and 0.877 (Max1, Var2) for Artificial Neural Network classifiers.

TABLE 3

Classification Results

| | Logistic Regression | | ANN 2 × 3 × 2 | | SVM Linear Kernel | |
|---|---|---|---|---|---|---|
| Features | Accuracy | F-Score | Accuracy | F-Score | Accuracy | F-Score |
| Max 1, Max 2 | 0.882 | 0.882 | 0.824 | 0.824 | 0.706 | 0.706 |
| Max 1, Var 2 | 0.765 | 0.760 | 0.882 | 0.882 | 0.706 | 0.700 |

Figure 10:
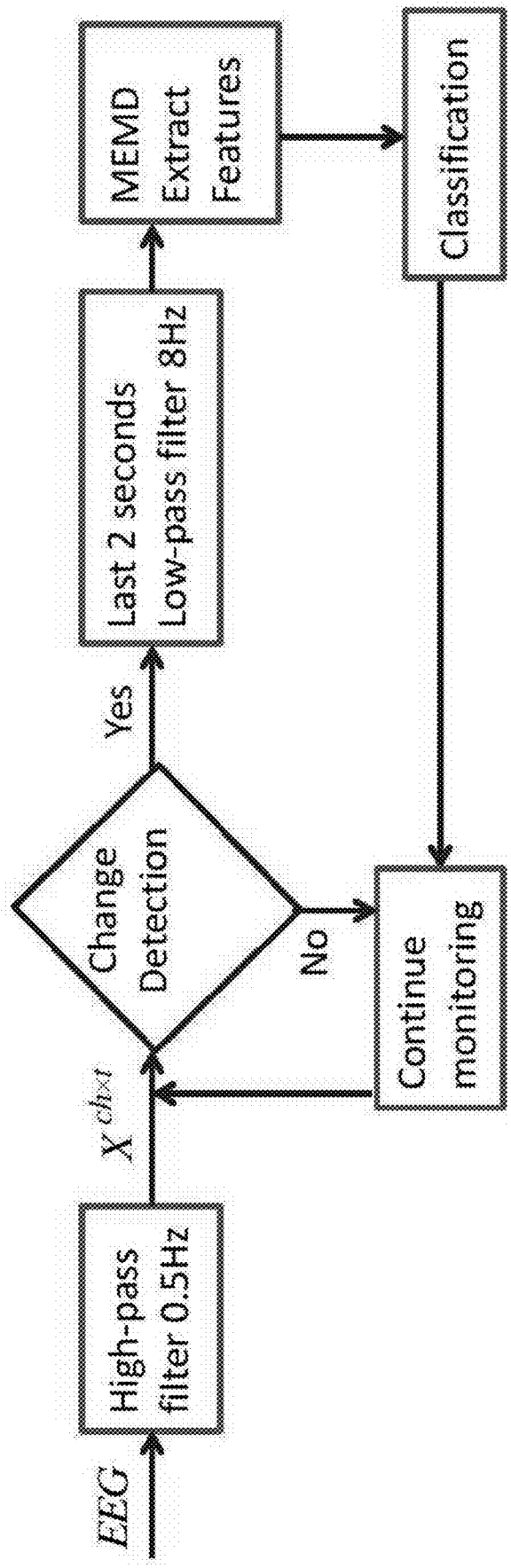
FIG. 10 shows a prediction process using discriminant functions.

Real-time prediction follows the procedure in FIG. 10. First, the signal is passed through a high-pass Butterworth filter of 0.5 Hz to remove the DC offset. The cleaned signal is monitored in real-time by eq. (1) and eq. (2) computed across channels at 32 Hz. Upon detection of a change in the eye state, the last two seconds of the 128 Hz signal is passed through a low-pass filter of 8 Hz to include only the eye movement artifact. The filtered signal is then passed through Multivariate Empirical Mode Decomposition and two features Max1 and Max2 are extracted that are based on the first and the second IMFs. The features are then fed to a logistic regression classifier to predict the eye state. The monitoring then continues. The proposed algorithm detects an eye state change in less than two seconds from its happening and continues monitoring right after a decision is made regarding the eye state. Thus, a delay of two seconds at most in detection is expected but the monitoring catches up afterwards. The procedure needs calibration before utilization.

While Rösler and Suendermann have used this dataset and achieved 97.3% accuracy using k-star classifier, their algorithm needs an average of 20 minutes to predict the eye state for new instances. Wang et al. and Sabanci and Koklu achieved accuracy of 76.6% and 84.05%, respectively through state of the art instance based algorithms. However, considering the sampling frequency of 128 Hz, the computations these classification procedure have to perform is huge, time consuming, and energy inefficient.

The methods described herein take the random nature of the eye state change into account and classification is applied only when a possible change of the eye state is detected using cross-channel information. The two procedures we proposed in this study take less than 2 seconds to predict an eye state change in real-time with 83.4% and 88.2% accuracy using a personal notebook with dual-core CPU 2.30 Hz and 2 GB RAM. A higher number of training examples could improve the accuracy of the classification procedures.

Having access to only one participant was a study limitation. However, this does not belittle the study and applicability of its results. The proposed analytical procedure could also be used with medical grade EEG devices and for new participants after adjustments for monitoring thresholds. Real applications require recording and investigation of the signals under real-life situations so that the signals include environmental artifacts. However, the controlled experimental situations are not simplistic trials and considered a step toward achieving the ultimate goal.

The analytics utilized in modeling multivariate brain signals can be adopted to analyze other biomedical signals and time series data in real-time. The process control monitors the input for potential change. Upon detection of a possible change, a fully data driven analytic steps are used to extract discriminant features from the segmented input signal. Then, machine learning analytics such as Logistic Regression, Artificial Neural Network (ANN), and Support Vector machine (SVM) are employed to verify the change.

The analytic findings have been employed in detecting the three different dance moves that honey bees perform to communicate the location of a food source. The findings are presented in the next chapter. Other applications of our analytic findings are Real-time epileptic seizure prediction using brain signals where early detection and prediction might be able to abort seizures through targeted therapies or could prevent accidents and limit injury.

Monitoring Market price for a significant change of patterns, then employing machine learning for making decisions upon detecting potential change.

Detecting Change of Motion through video or biomedical signals achievable by monitoring for a possible change and then using machine learning when a possible change happens.

Autonomous cars to continue a former pattern unless a significant change in the conditions has taken place.

Application in Modeling Honey Bee Dance

Honey bees perform special dances within the beehive to communicate the location of food sources. Usually, each dance pattern consists of two phases. The waggle phase during which the bee walks roughly in a straight line while rapidly shaking its body from left to right and the turning phase at the endpoint of a waggle dance in which the bee typically returns to the starting location of the waggle dance by turning in a clockwise (right) or counterclockwise (left) direction. The direction and duration of waggle dance conveys the direction and distance of the food source, respectively. For example, flowers that are located directly in line with the sun are represented by waggle runs in an upward direction on the vertical combs, and any angle to the right or left of the sun is coded by a corresponding angle to the right or left of the upward direction; see FIG. 11.

The Australian scientist Karl von Frisch was the first who discovered how honeybees communicate the location of the food source through dancing and was honored with a Nobel Prize in 1973 for his discovery. Honey bees even adjust their flight path to compensate for being blown off course by the wind and for changing position of the sun through time. However, their course is seldom so precise that they can find the food without the aid of vision and/or smell as they approach it.

The aim of this disclosure is to use the approach discussed above with respect to eye state changes to classify the dance patterns with high accuracy in real-time. That is, to utilize a monitoring function, then apply classification upon observing a potential change in the dance move.

Figure 11:
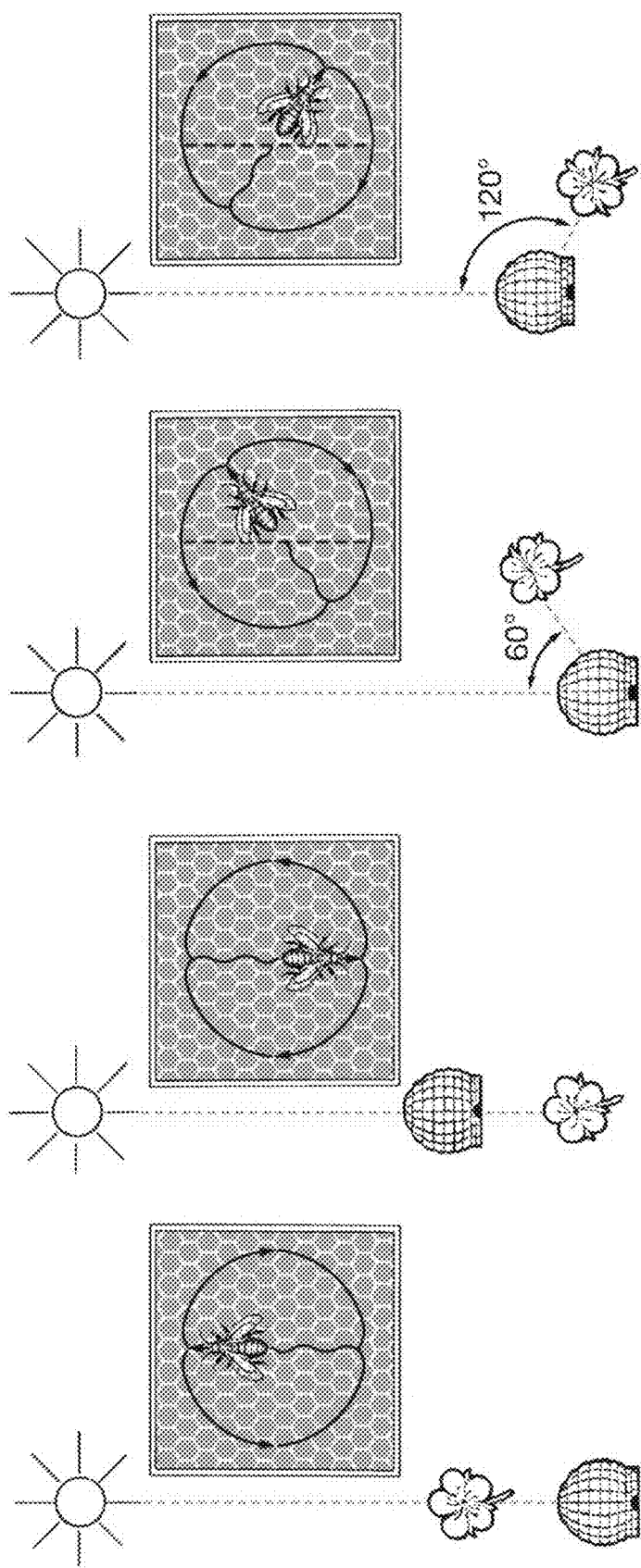
FIG. 11 shows a honeybee dance that indicates a location of a food source.
Figure 12:
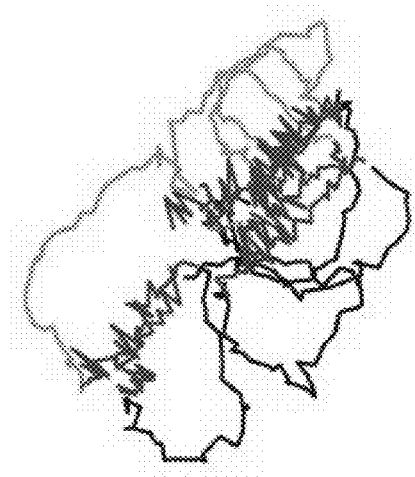
FIG. 12 shows honeybee dance patterns for turn-right, turn-left, and waggle.
Figure 12:
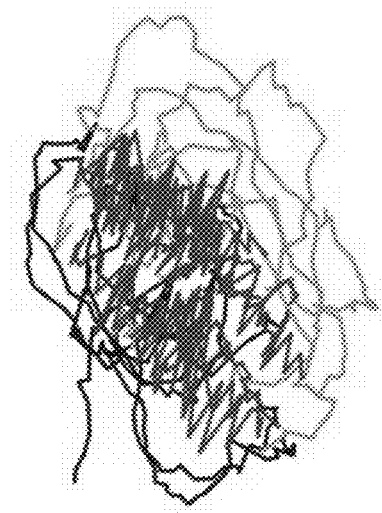
Figure 12:
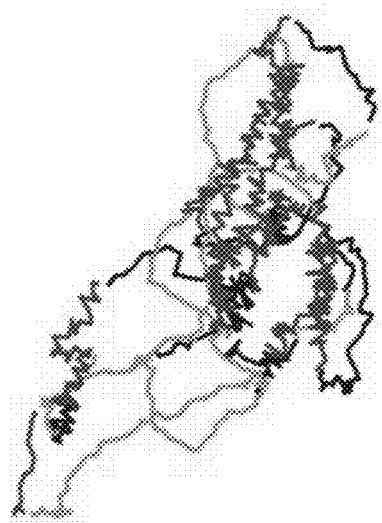

A dataset for honey bee dance can be found in where there are six set of measurements $x_t=(x_t, y_t, \theta_t, c_t)$ in which $(x_t, y_t)$ denotes the 2D coordinates of the bee's body in x and y axis at time t, $\theta_t$ represents the bee's head angle, and $c_t$ shows the ground truth or label of the dance move; c=−1 for turn-right, c=0 for turn-left, c=1 for waggle. The dance label has been added later by investigating a video feed that was focused on the honey combs. FIG. 11 displays three such sequences of honey bee dances. Researchers have tried to model the honey bee dance patterns using various methods in order to understand the communication aspect and to mimic that pattern in building intelligent robots. Yet after 60 years of discovering the waggle dance it is unknown how a follower bee decodes the information contained in the dance. Moreover, researchers still use the time-consuming and error-prone process of human labeling to segment dance patterns.

Oh et al., Xuan and Murphy, and Fox have used switching dynamical models to analyze these honey bee dances. In particular, Oh et al. (2006) have used Switching Linear Dynamic System (SLDS) in a supervised hold-one-out formulation and Parameterized Segmental SLDS which requires additional supervising during the learning process to achieve high model accuracy. Xuan and Murphy (2008) have segmented the overall signal into patterns of dance moves using a first-order Auto-Regressive AR(1) model, using independent features or with a full covariance model. Fox (2010) have used sticky Hidden Markov Model (HMM) with Hierarchical Dirichlet processes (HDP) and switching Vector Autoregressive (VAR) in both unsupervised and partially supervised setting to model the dance patterns. Table 4 shows accuracy of these approaches for each dancing bee.

TABLE 4

| Model accuracy | | | | | | |
|---|---|---|---|---|---|---|
| | Bee# | | | | | |
| | 1 | 2 | 3 | 4 | 5 | 6 |
| HDP-VAR(1)-HMM unsupervised | 45.0 | 42.7 | 47.3 | 88.1 | 92.5 | 88.2 |
| HDP-VAR(1)-HMM partially supervised | 55.0 | 86.3 | 81.7 | 89.0 | 92.4 | 89.6 |
| SLDS supervised MCMC | 74.0 | 86.1 | 81.3 | 93.4 | 90.2 | 90.4 |
| PS-LDS supervised MCMC | 75.9 | 92.4 | 83.1 | 93.4 | 90.4 | 91.0 |

Although, the above methods seems to achieve a high model accuracy through sophisticated modeling, we believe a simpler model that runs fast and does not require extensive training is favorable in real applications. This can be achieved through monitoring and then classifying only when a potential change is observed.

Figure 13:
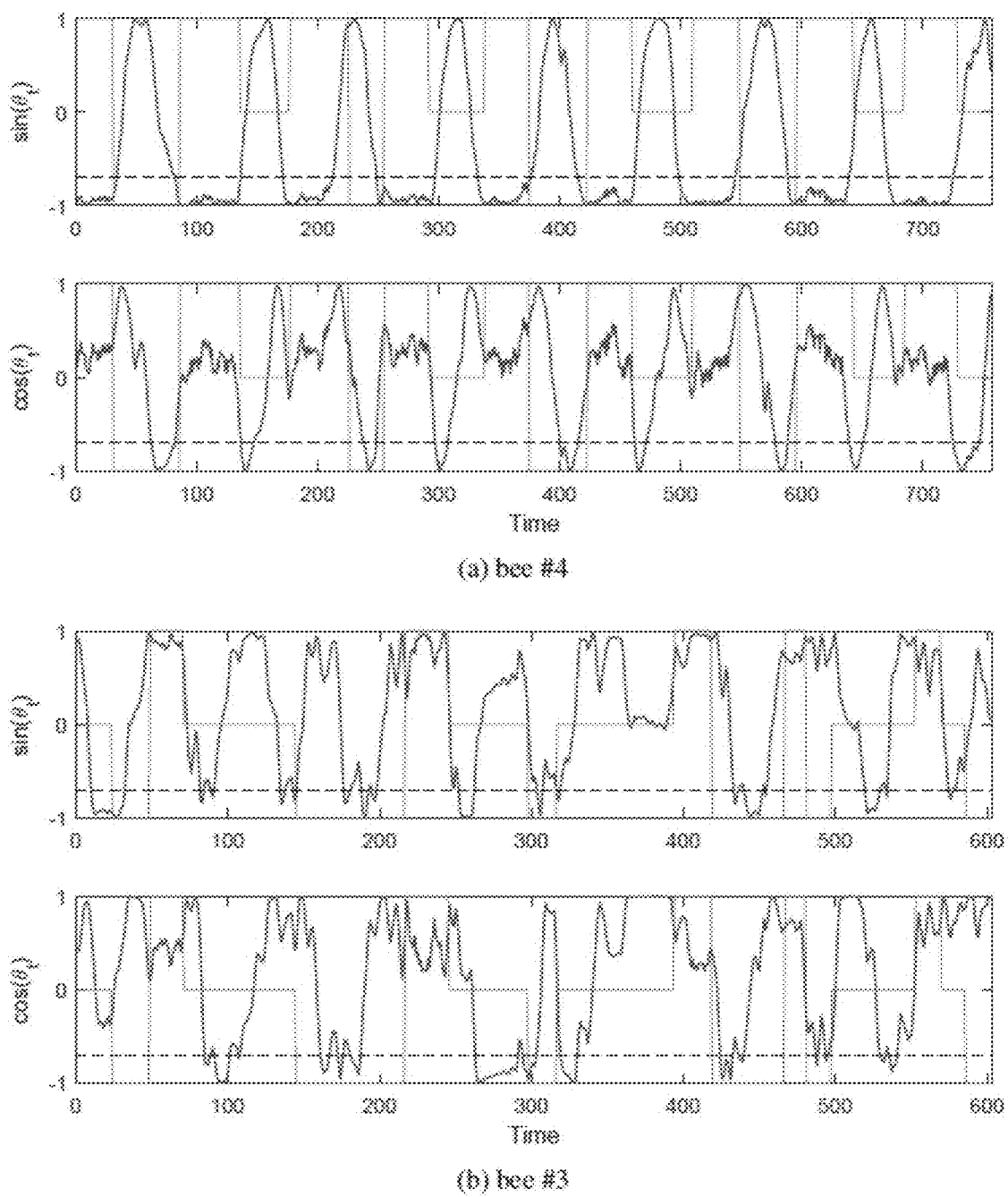
FIG. 13 shows monitoring functions for the honeybee dance.

After investigating some statistical characteristics of the dance signals such as variance, average, minimum, maximum, moving mean and variance we arrived at the conclusion that a moving average of sin(θ$_t$) with window size 3 can efficiently signal for a change of dance pattern. The moving average of 3 smooths the sharp edges of a signal and helps with detecting steady increase/decrease. FIG. 13 a shows how setting a threshold on sin(θ$_t$) can segment the overall dance signal into intervals of patterns for bee #4. The threshold was set as −0.7 which could detect all the change dance patterns with some lags at the time they happened. The same pattern could be seen in bee #5 and #6 but it was less tractable in bees #1, #2, and #3. The utilized head angle signals have been normalized to reflect the direction toward 12:00.

By comparing the dance patterns of bee #3 and bee #4 in FIG. 13, it is realized there are some intervals that logically do not match with the provided label for bee #3. This issue has been mentioned in the literature as well. We were unable to determine how the labels were assigned to the overall signal but we could find the videos related to the dance moves. However, the files were not the original recordings and low quality of the videos made it impossible to find the true dance patterns. Thus, the dance patterns of bees #4 to #6 were analyzed that seemed to have little to no discrepancy.

Figure 14:
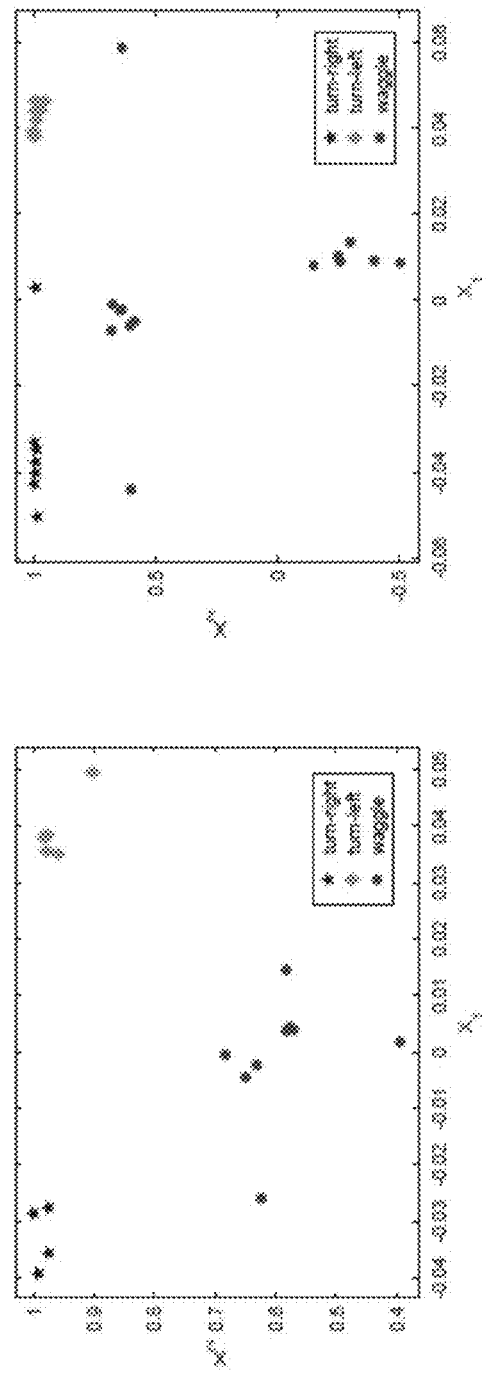
FIG. 14 shows two selected features for the honeybee dance, and their values.
Figure 14:
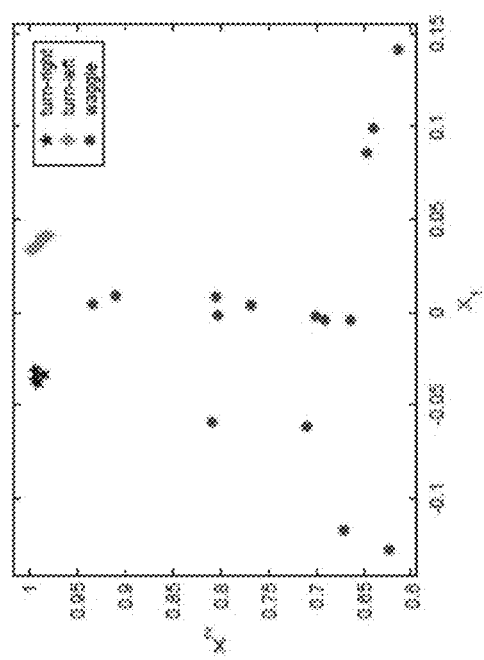

Next step was the feature extraction in which discriminant features were found to classify three different dance moves. Starting by bee #4 and after positive feedback applied the same technique to other bees. For bee #4, after segmenting the continuous signal into 18 intervals of various sizes based on the results of the monitoring section, we extracted various numbers from each interval as potential features. For the head angle θ$_t$, these features included variance, mean, minimum, and maximum of sin(θt), cos(θt), MovAve(sin(θt), 3), MovAve(cos(θt), 3), Diff (MovAve(sin(θt), 3)), Diff (MovAve(cos(θt), 3)), etc. computed over a given interval t ∈ T. After investigating the matrix scatter plot of the extracted features, $X_1$: mean of the Diff (MovAve(cos(θt), 3)) and $X_2$: maximum of MovAve(cos(θt), 3) were used as features. FIG. 14 (see graph (a)) best shows the reason for this decision. Obviously, this choice significantly discriminates the three dance patterns.

Going over the same process of monitoring using moving average of sin(θt), utilizing a threshold of −0.7 for detecting potential change of dance pattern, segmenting the continuous recording signal using the monitoring section, and extracting the two features $X_1$ and $X_2$ for bees #5 and #6 resulted in scatter plot of features illustrated in FIG. 14 (see graph (b) and graph (c)), respectively. Like before, the segmented intervals are well discriminated using the two utilized features. This will result in great classification performance in the next step.

In this step, the features are fed to three classification methods known as Logistic Regression, Artificial Neural Network, and Support Vector Machine. Weka software has been used to perform the classifications with a 5-fold cross validation. Table 5 provides the accuracy and F-score of classifying the bee dance patterns using our approach for different bees. The advantages of this approach are:

High classification accuracy that reaches to approximately 100% for some cases that beats alternate approaches in the literature.
Fast run time of the procedure, it runs in fractions of a second, which makes it suitable for real-time and real-life predictions.
Simplicity of the proposed process
Possibility of pooling the samples together for higher classification accuracy.

As seen in Table 5, the extracted features are pooled together and then classification is performed. This improves the reliability of the results since there are more training samples.

TABLE 5

Classification Accuracy and F-score

| Bee # | | 4 | 5 | 6 | 4-6 |
|---|---|---|---|---|---|
| Logistic Regression | Accuracy | 94.4 | 100. | 87.0 | 97.1 |
| | F-score | 94.6 | 100. | 87.0 | 97.2 |
| ANN 2 × 3 × 3 | Accuracy | 100. | 100. | 73.9 | 92.9 |
| | F-score | 100. | 100. | 69.3 | 93.0 |
| SVM RBF Kernel | Accuracy | 100. | 81.5 | 66.2 | 98.6 |
| | F-score | 100. | 76.3 | 52.5 | 98.6 |

Figure 15:
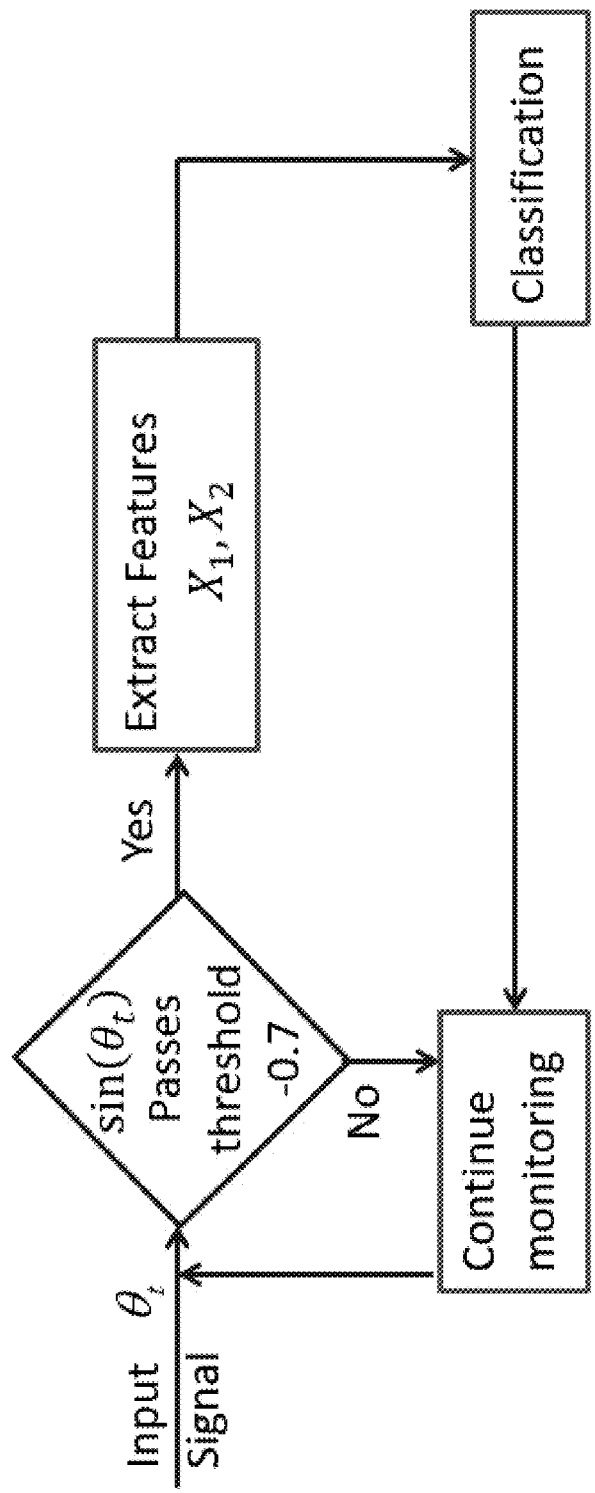
FIG. 15 shows a honeybee real-time application circuit.

The decision circuit process given in FIG. 15 was utilized. First, the normalized head angle signal θ$_t$ is monitored in real time by sin(θ$_t$) computed at 30 Hz frequency. Upon passing a threshold of −0.7, the available signal is used to extract two features $X_1$, $X_2$. The features are then fed to a selected classifier, we recommend ANN, to predict the type of dance movement. The monitoring then continues for the remainder of the signal. The procedure needs calibration before applying.

Studying honey bee dance patterns requires expert-labeling of videotapes which is a time-consuming and error prone process. As seen in this application, the monitoring-action process significantly improves the processing time of classifying signals and could replace the time-consuming and error-prone stage of expert labeling.

Various features and advantages of the invention are set forth in the following claims.

What is claimed is:
1. A method for detecting a random state change in a physical subject, the method comprising:
receiving, using one or more electronic processors, a plurality of multivariate signals via a respective plurality of physical channels, wherein the plurality of multivariate signals comprise information about the state change in the physical subject, wherein the plurality of multivariate signals are sampled at a specified sampling rate;
monitoring, using the one or more electronic processors, values of statistical characteristics of the plurality of multivariate signals;
detecting, using the one or more electronic processors, a potential change of state in the physical subject when the monitored statistical characteristics values of at least one of the plurality of multivariate signals exceed a threshold;
low-pass filtering, using the one or more electronic processors, a time interval of the plurality of multivariate signals that precedes the detected potential change of state in the physical subject to generate a respective plurality of state change artifact signals;
simultaneously decomposing, using the one or more electronic processors, the plurality of state change artifact signals by multivariate empirical mode decomposition and generating a plurality of intrinsic mode functions;
extracting, using the one or more electronic processors, features from one or more of the plurality of intrinsic mode functions;
providing, using the one or more electronic processors, the extracted features to a logistic regression classifier;

repeating the steps of monitoring, detecting, low-pass filtering, decomposing, extracting, and providing the extracted features to the logistic regression classifier; and predicting, using the one or more electronic processors, a state of the physical subject using the logistic regression classifier.

2. The method of claim 1, wherein the plurality of multivariate signals are high pass filtered to remove DC components of the plurality of multivariate signals prior to the monitoring of the values of the statistical characteristics of the plurality of multivariate signals.

3. The method of claim 1, wherein the plurality of multivariate signals comprise electroencephalogram (EEG) signals, and wherein the physical subject is an eye and potential states of the eye include an open state and a closed state.

4. The method of claim 1, wherein the plurality of multivariate signals are nonlinear and non-stationary signals.

5. The method of claim 1, wherein the statistical characteristics of the plurality of multivariate signals include maximum and minimum values of the plurality of multivariate signals.

6. The method of claim 1, wherein the statistical characteristics of the plurality of multivariate signals are monitored at a reduced rate relative to the sampling rate.

7. The method of claim 1, wherein the plurality of multivariate signals comprise electroencephalogram (EEG) signals, and wherein the respective plurality of state change artifact signals are eye opening or eye closing artifact signals.

8. The method of claim 1, wherein the features are extracted from the one or more of the plurality of intrinsic mode functions over a reduced time interval relative to the time interval that precedes the detected potential change of state in the physical subject.

9. The method of claim 1, wherein the features are extracted from the one or more of the plurality of intrinsic mode functions over a reduced time interval relative to the time interval that precedes the detected potential change of state in the physical subject, using a common spatial pattern method.

10. The method of claim 1, wherein the features are extracted from the one or more of the plurality of intrinsic mode functions over a reduced time interval relative to the time interval that precedes the detected potential change of state in the physical subject, based on values of discriminant features of the one or more of the plurality of intrinsic mode functions.

11. A system for detecting a random state change in a physical subject, the system comprising:
a memory storing program instructions; and
an electronic processor coupled to the memory, the electronic processor, through retrieval and execution of the program instructions, configured to:
receive a plurality of multivariate signals via a respective plurality of physical channels, wherein the plurality of multivariate signals comprise information about the state change in the physical subject, wherein the plurality of multivariate signals are sampled at a specified sampling rate;
monitor values of statistical characteristics of the plurality of multivariate signals;
detect a potential change of state in the physical subject when the monitored statistical characteristics values of at least one of the plurality of multivariate signals exceed a threshold;
low-pass filter a time interval of the plurality of multivariate signals that precedes the detected potential change of state in the physical subject to generate a respective plurality of state change artifact signals;
simultaneously decompose the plurality of state change artifact signals by multivariate empirical mode decomposition and generate a plurality of intrinsic mode functions;
extract features from one or more of the plurality of intrinsic mode functions;
provide the extracted features to a logistic regression classifier;
repeat the steps of monitoring, detecting, low-pass filtering, decomposing, extracting, and providing the extracted features to the logistic regression classifier; and
predict a state of the physical subject using the logistic regression classifier.

12. The system of claim 11, wherein the plurality of multivariate signals are high pass filtered to remove DC components of the plurality of multivariate signals prior to the monitoring of the values of the statistical characteristics of the plurality of multivariate signals.

13. The system of claim 11, wherein the plurality of multivariate signals comprise electroencephalogram (EEG) signals, and wherein the physical subject is an eye and potential states of the eye include an open state and a closed state.

14. The system of claim 11 wherein the plurality of multivariate signals are nonlinear and non-stationary signals.

15. The system of claim 11, wherein the statistical characteristics of the plurality of multivariate signals include maximum and minimum values of the plurality of multivariate signals.

16. The system of claim 11, wherein the statistical characteristics of the plurality of multivariate signals are monitored at a reduced rate relative to the sampling rate.

17. The system of claim 11, wherein the plurality of multivariate signals comprise electroencephalogram (EEG) signals, and wherein the respective plurality of state change artifact signals are eye opening or eye closing artifact signals.

18. The system of claim 11, wherein the features are extracted from the one or more of the plurality of intrinsic mode functions over a reduced time interval relative to the time interval that precedes the detected potential change of state in the physical subject.

19. The system of claim 11, wherein the features are extracted from the one or more of the plurality of intrinsic mode functions over a reduced time interval relative to the time interval that precedes the detected potential change of state in the physical subject, using a common spatial pattern method.

20. The system of claim 11, wherein the features are extracted from the one or more of the plurality of intrinsic mode functions over a reduced time interval relative to the time interval that precedes the detected potential change of state in the physical subject, based on values of discriminant features of the one or more of the plurality of intrinsic mode functions.

* * * * *